United States Patent
Tsao et al.

(10) Patent No.: US 10,302,640 B2
(45) Date of Patent: May 28, 2019

(54) IMAGE DIFFERENTIATED MULTIPLEX ASSAYS

(71) Applicant: PLEXBIO CO., LTD., Taipei (TW)

(72) Inventors: Dean Tsao, Hillsborough, CA (US); Chin-Shiou Huang, Santa Clara, CA (US); Yao-Kuang Chung, New Taipei (TW)

(73) Assignee: PLEXBIO CO., LTD., Taipei (TW)

( * ) Notice: Subject to any disclaimer, the term of this patent is extended or adjusted under 35 U.S.C. 154(b) by 0 days.

(21) Appl. No.: 15/374,930

(22) Filed: Dec. 9, 2016

(65) Prior Publication Data

US 2017/0160272 A1     Jun. 8, 2017

Related U.S. Application Data

(63) Continuation of application No. PCT/IB2016/000937, filed on Jun. 10, 2016.
(Continued)

(51) Int. Cl.
| | | |
|---|---|---|
| *G01N 33/553* | (2006.01) | |
| *G01N 33/545* | (2006.01) | |
| *G01N 33/543* | (2006.01) | |
| *C12Q 1/6813* | (2018.01) | |
| *C12Q 1/6816* | (2018.01) | |
| *C12Q 1/6834* | (2018.01) | |

(52) U.S. Cl.
CPC ......... *G01N 33/545* (2013.01); *C12Q 1/6813* (2013.01); *C12Q 1/6816* (2013.01); *C12Q 1/6834* (2013.01); *G01N 33/54326* (2013.01); *G01N 33/54393* (2013.01); *G01N 33/553* (2013.01)

(58) Field of Classification Search
CPC .......... G01N 33/545; G01N 33/54393; G01N 33/33553; C12Q 1/6816; C12Q 1/6834
USPC .......................................................... 422/402
See application file for complete search history.

(56) References Cited

U.S. PATENT DOCUMENTS

| 7,858,307 B2 | 12/2010 | Ho |
| 7,871,770 B2 | 1/2011 | Ho |

(Continued)

FOREIGN PATENT DOCUMENTS

| CN | 1271410 C | 8/2006 |
| CN | 102246037 B | 5/2014 |

(Continued)

OTHER PUBLICATIONS

Braeckmans et al., "Encoding Microcarriers: Present and Future Technologies", Nature Reviews Drug Discovery, vol. 1, Jun. 2002, pp. 447-456.

(Continued)

*Primary Examiner* — Jill A Warden
*Assistant Examiner* — Jacqueline Brazin
(74) *Attorney, Agent, or Firm* — Morrison and Foerster LLP

(57) ABSTRACT

Provided herein are encoded microcarriers for analyte detection in multiplex assays. The microcarriers are encoded with an analog code for identification and include a capture agent for analyte detection. Also provided are methods of making the encoded microcarriers disclosed herein. Further provided are methods and kits for conducting a multiplex assay using the microcarriers described herein.

28 Claims, 24 Drawing Sheets

Related U.S. Application Data

(60) Provisional application No. 62/174,401, filed on Jun. 11, 2015.

(56) References Cited

U.S. PATENT DOCUMENTS

| | | | |
|---|---|---|---|
| 8,148,139 B2 | 4/2012 | Ho | |
| 8,232,092 B2 | 7/2012 | Ho et al. | |
| 8,610,848 B2 | 12/2013 | Shim et al. | |
| 8,697,334 B2 | 4/2014 | True et al. | |
| 8,939,376 B1 | 1/2015 | De Smedt et al. | |
| 8,967,483 B2 | 3/2015 | De Smedt et al. | |
| 9,040,463 B2 | 5/2015 | Demierre et al. | |
| 9,063,044 B2 | 6/2015 | Kao et al. | |
| 9,255,922 B2 | 2/2016 | Ho et al. | |
| 2006/0097056 A1 | 5/2006 | De Smedt et al. | |
| 2008/0234144 A1 | 9/2008 | Ho et al. | |
| 2009/0201504 A1 | 8/2009 | Ho et al. | |
| 2010/0075438 A1 | 3/2010 | Ho et al. | |
| 2010/0081215 A1* | 4/2010 | De Geest | G01N 33/54326 436/518 |
| 2010/0210477 A1 | 8/2010 | Ho | |
| 2011/0007955 A1 | 1/2011 | Ho et al. | |
| 2012/0088691 A1 | 4/2012 | Chen et al. | |
| 2012/0200950 A1* | 8/2012 | Shim | G02B 5/201 359/891 |
| 2013/0095574 A1* | 4/2013 | Demierre | B81C 99/008 436/501 |
| 2013/0302910 A1* | 11/2013 | Demierre | B01L 3/502761 436/501 |
| 2014/0274778 A1 | 9/2014 | Tsao et al. | |
| 2015/0057190 A1 | 2/2015 | De Smedt et al. | |
| 2015/0190803 A1* | 7/2015 | Demierre | B01L 3/502707 506/39 |

FOREIGN PATENT DOCUMENTS

| | | |
|---|---|---|
| EP | 1173760 B1 | 6/2005 |
| EP | 2100143 A1 | 9/2009 |
| EP | 2179289 A1 | 4/2010 |
| EP | 2342561 A1 | 7/2011 |
| EP | 2367633 A1 | 9/2011 |
| EP | 2484447 A1 | 8/2012 |
| EP | 2673086 A1 | 12/2013 |
| EP | 1903337 B1 | 7/2015 |
| WO | 2000/63695 A1 | 10/2000 |
| WO | 2002/059603 A2 | 8/2002 |
| WO | 2008/034275 A1 | 3/2008 |
| WO | 2009/020506 A1 | 2/2009 |
| WO | 2009/128938 A1 | 10/2009 |
| WO | 2010/042745 A1 | 4/2010 |
| WO | 2010/072011 A1 | 7/2010 |
| WO | 2011/014879 A2 | 2/2011 |
| WO | 2011/156432 A2 | 12/2011 |
| WO | 2012/106827 A1 | 8/2012 |
| WO | 2014/031997 A1 | 2/2014 |
| WO | 2014/144016 A1 | 9/2014 |
| WO | 2016/198954 A1 | 12/2016 |

OTHER PUBLICATIONS

Chung et al., "U.S. App. No. 15/358,024, filed Nov. 21, 2016, titled Methods and Systems for Selection of Detection Area".

Derveaux et al., "Layer-by-Layer Coated Digitally Encoded Microcarriers for Quantification of Proteins in Serum and Plasma", Analytical Chemistry, Dec. 4, 2007, pp. 85-94.

International Search Report and Written Opinion received for PCT Patent Application No. PCT/IB2016/000937, dated Oct. 27, 2016, 7 pages.

Bong et al., "Magnetic Barcoded Hydrogel Microparticles for Multiplexed Detection", Langmuir, vol. 26, No. 11, 2010, pp. 8008-8014.

Extended European Search Report (includes Supplementary European Search Report and European Search Opinion) received for European Patent Application No. 16806958.1, dated Sep. 25, 2018, 8 pages.

* cited by examiner

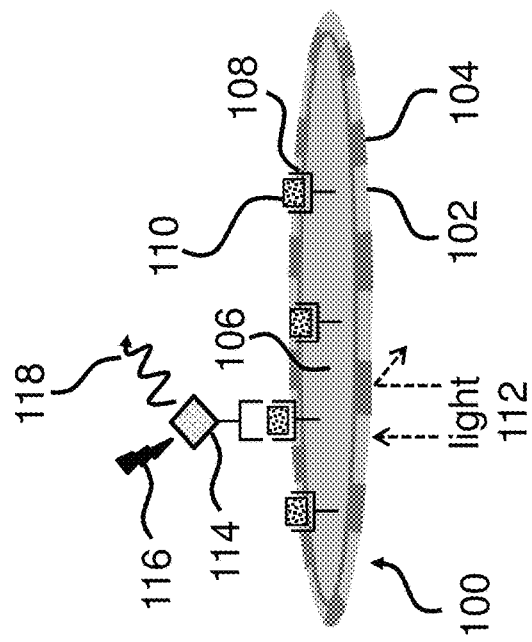
FIG. 1D
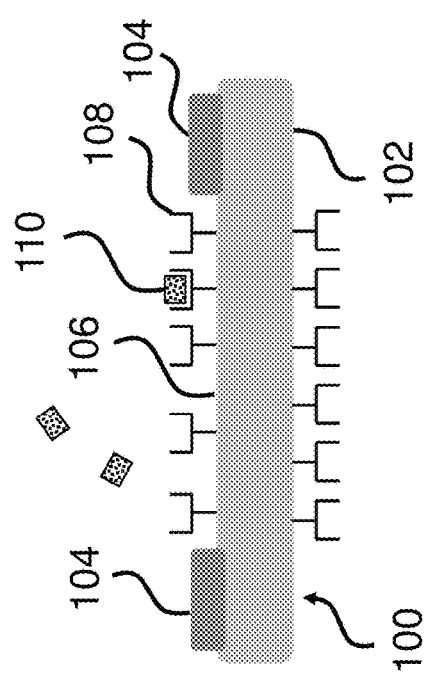
FIG. 1C
FIGS. 1C & 1D

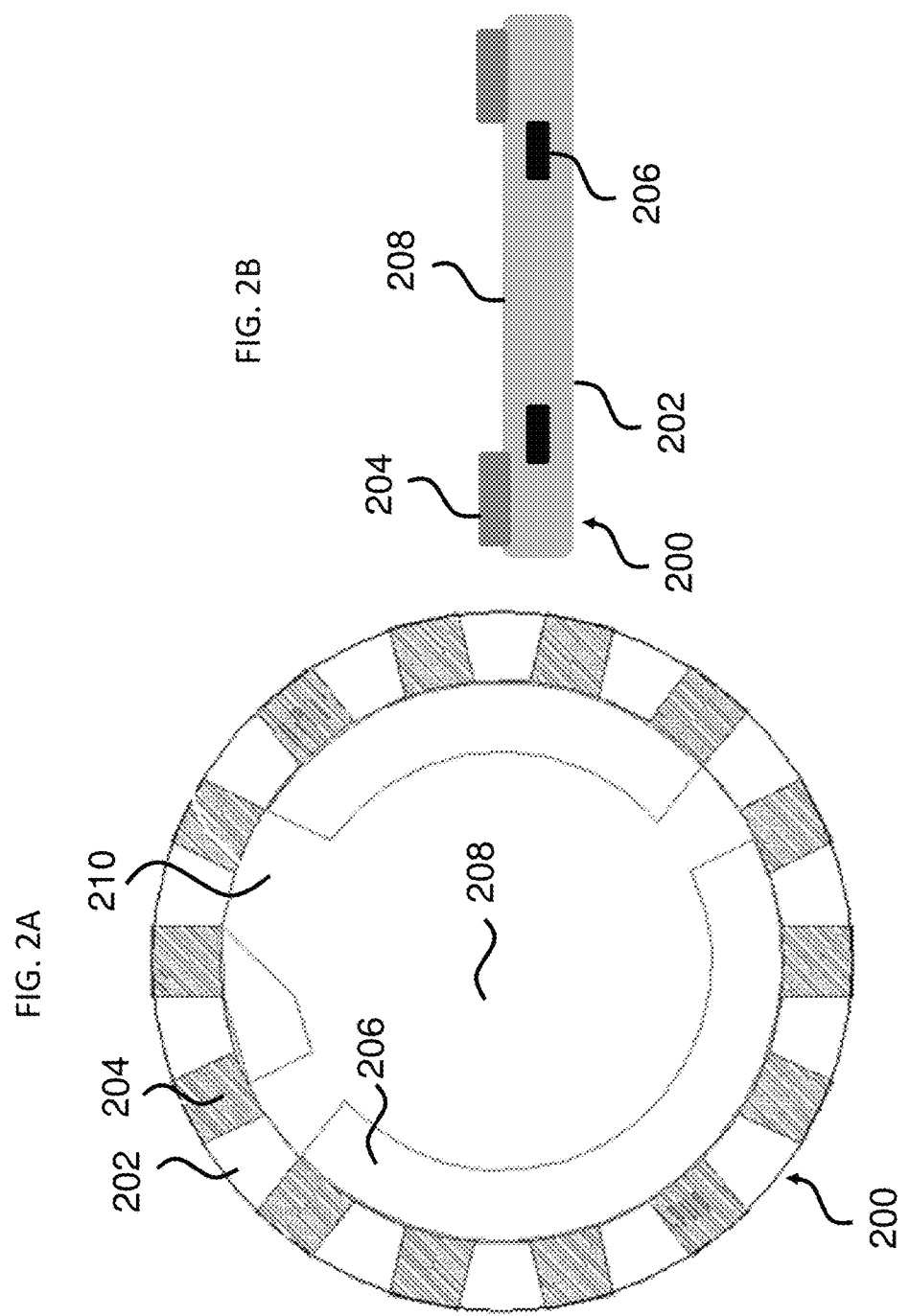

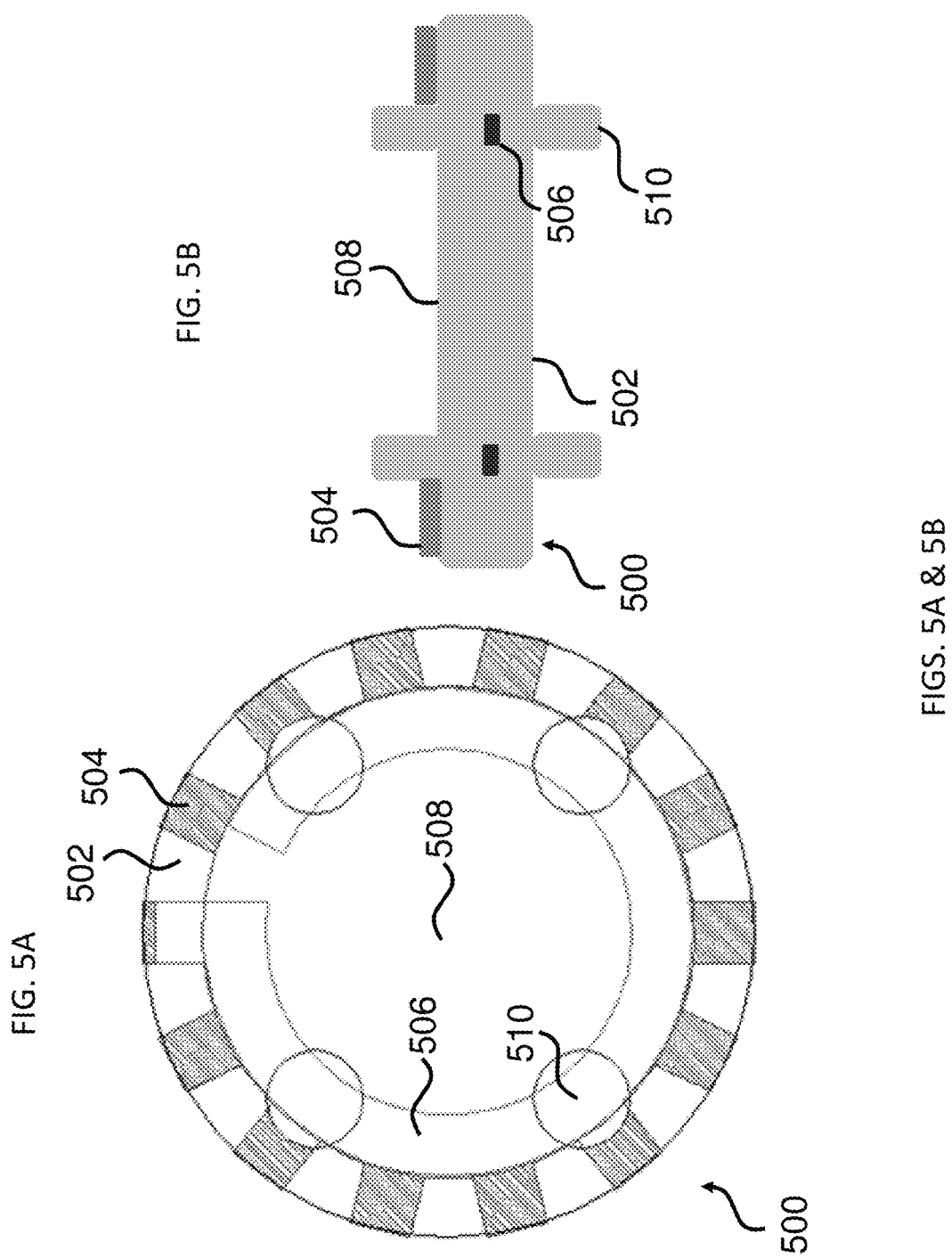

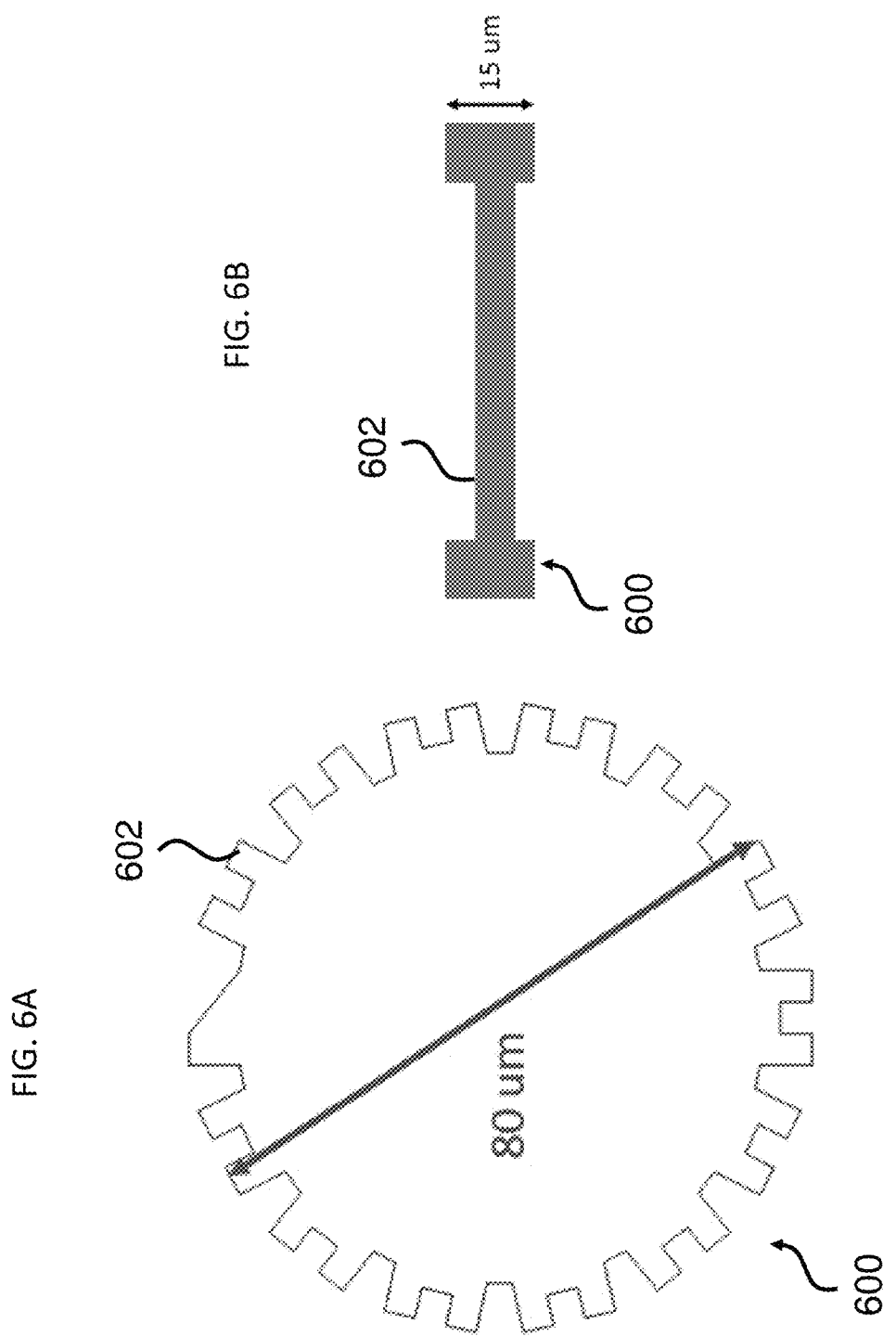

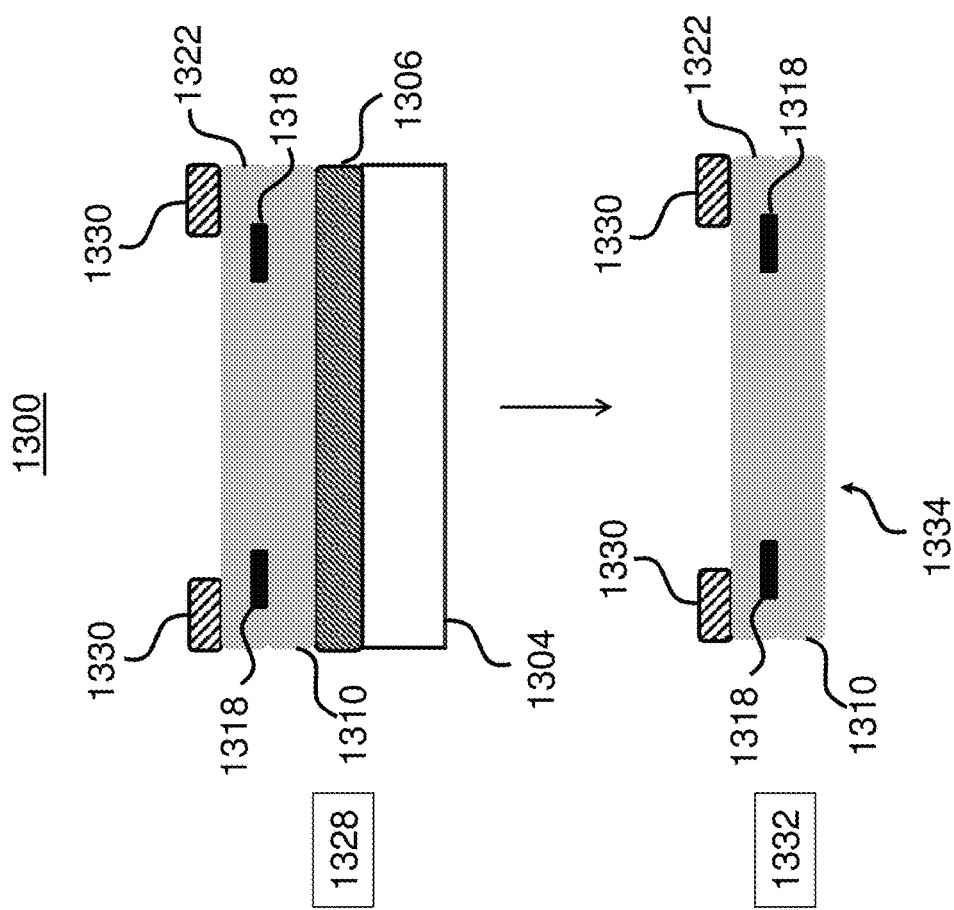

IMAGE DIFFERENTIATED MULTIPLEX ASSAYS

This application is a continuation of International Application No. PCT/IB2016/000937, filed internationally on Jun. 10, 2016, which claims the priority benefit of U.S. Provisional Application Ser. No. 62/174,401, filed Jun. 11, 2015, the disclosures of both of which are herein incorporated by reference in their entirety.

FIELD

Provided herein are encoded microcarriers for analyte detection in multiplex assays, as well as methods of making and using the same and kits related thereto. The microcarriers are encoded with an analog code for identification and include a capture agent for capturing an analyte.

BACKGROUND

Immunological and molecular diagnostic assays play a critical role both in the research and clinical fields. Often it is necessary to perform assays for a panel of multiple targets to gain a meaningful or bird's-eye view of results to facilitate research or clinical decision-making. This is particularly true in the era of genomics and proteomics, where an abundance of genetic markers and/or biomarkers are thought to influence or be predictive of particular disease states. In theory, assays of multiple targets can be accomplished by testing each target separately in parallel or sequentially in different reaction vessels (i.e., multiple singleplexing). However, not only are assays adopting a singleplexing strategy often cumbersome, but they also typically required large sample volumes, especially when the targets to be analyzed are large in number.

A multiplex assay simultaneously measures multiple analytes (two or more) in a single assay. Multiplex assays are commonly used in high-throughput screening settings, where many specimens can be analyzed at once. It is the ability to assay many analytes simultaneously and many specimens in parallel that is the hallmark of multiplex assays and is the reason that such assays have become a powerful tool in fields ranging from drug discovery to functional genomics to clinical diagnostics. In contrast to singleplexing, by combining all targets in the same reaction vessel, the assay is much less cumbersome and much easier to perform, since only one reaction vessel is handled per sample. The required test samples can thus be dramatically reduced in volume, which is especially important when samples (e.g., tumor tissues, cerebral spinal fluid, or bone marrow) are difficult and/or invasive to retrieve in large quantities. Equally important is the fact that the reagent cost can be decreased and assay throughput increased drastically.

Many assays of complex macromolecule samples are composed of two steps. In the first step, agents capable of specifically capturing the target macromolecules are attached to a solid phase surface. These immobilized molecules may be used to capture the target macromolecules from a complex sample by various means, such as hybridization (e.g., in DNA, RNA based assays) or antigen-antibody interactions (in immunoassays). In the second step, detection molecules are incubated with and bind to the complex of capture molecule and the target, emitting signals such as fluorescence or other electromagnetic signals. The amount of the target is then quantified by the intensity of those signals.

Multiplex assays may be carried out by utilizing multiple capture agents, each specific for a different target macromolecule. In chip-based array multiplex assays, each type of capture agent is attached to a pre-defined position on the chip. The amount of multiplex targets in a complex sample is determined by measuring the signal of the detection molecule at each position corresponding to a type of capture agent. In suspension array multiplex assays, microparticles or microcarriers are suspended in the assay solution. These microparticles or microcarriers contain an identification element, which may be embedded, printed, or otherwise generated by one or more elements of the microparticle/microcarrier. Each type of capture agent is immobilized to particles with the same ID, and the signals emitted from the detection molecules on the surface of the particles with a particular ID reflect the amount of the corresponding target.

Existing systems for suspension array multiplex assays are limited in resolution. Some multiplex systems use digital barcodes printed on flat microbeads using standard semiconductor fabrication techniques. However, the number of identifiers that can be generated by a particular number of digits is limited. Increasing the number of unique identifiers requires increasing the number of barcode digits, thus requiring more space for printing on an already tiny microbead. Another type of multiplex system uses color-coding, such as fluorescent beads encoded with a unique fluorescent dye. However, the number of unique identifiers available for such fluorescent systems is limited due to overlapping excitation/emission spectra, and identification errors may arise from, e.g., batch-to-batch variation in fluorescent dyes.

Therefore, a need exists for an analog-encoded multiplex assay system, e.g., one not constrained by limitations such as digital barcode size or fluorophore resolution. Such a system allows nearly unlimited unique identifiers and minimizes recognition error due to the use of analog codes (e.g., from overlapping spectra or batch-to-batch fluorophore variation).

All publications, patents, and patent applications cited herein are hereby incorporated by reference in their entirety for all purposes.

BRIEF SUMMARY

To meet this need, provided herein, inter alia, are microcarriers, encoded with an analog code, that include a capture agent for capturing an analyte. These microcarriers may be used, for example, in multiplexed assays in which each microcarrier includes a capture agent for capturing a specific analyte and an analog code for identification. Methods of making and using such micocarriers, as well as kits related thereto, are further provided.

Accordingly, in one aspect, provided herein is an encoded microcarrier comprising (a) a substantially transparent polymer layer having a first surface and a second surface, the first and the second surfaces being parallel to each other; (b) a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code; and (c) a capture agent for capturing an analyte, wherein the capture agent is coupled to at least one of the first surface and the second surface of the substantially transparent polymer layer in at least the center portion of the substantially transparent polymer layer.

In some embodiments, the microcarrier further comprises (d) a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer. In some embodiments, the microcarrier further comprises (e) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (f) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the microcarrier further comprises an orientation indicator for orienting the analog code of the substantially non-transparent polymer layer. In some embodiments, the orientation indicator comprises an asymmetry of the magnetic, substantially non-transparent layer. In some embodiments, the magnetic, substantially non-transparent layer comprises nickel. In some embodiments, the magnetic, substantially non-transparent layer is between about 50 nm and about 10 µm in thickness. In some embodiments, the magnetic, substantially non-transparent layer is about 0.1 µm in thickness. In some embodiments, the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 µm and about 10 µm wide. In some embodiments, the plurality of gear teeth comprises one or more gear teeth that are between about 1 µm and about 10 µm tall. In some embodiments, the plurality of gear teeth comprises two or more gear teeth that are spaced between about 1 µm and about 10 µm apart. In some embodiments, the microcarrier further comprises (g) one or more columns projecting from the first surface of the first substantially transparent polymer layer, wherein the one or more columns are not within the center portion of the first substantially transparent polymer layer; and/or (h) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the microcarrier is a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the microcarrier is less than about 200 µm in diameter. In some embodiments, the microcarrier is about 50 µm in diameter. In some embodiments, the microcarrier is less than about 50 µm in thickness. In some embodiments, the microcarrier is about 10 µm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the capture agent for capturing the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially transparent polymer of the first or the second substantially transparent polymer layer comprises an epoxy-based polymer. In some embodiments, the epoxy-based polymer is SU-8.

In another aspect, provided herein is an encoded microcarrier comprising (a) a substantially non-transparent polymer layer having a first surface and a second surface, the first and the second surfaces being parallel to each other, wherein an outline of the substantially non-transparent polymer layer comprises a two-dimensional shape that represents an analog code; and (b) a capture agent for capturing an analyte, wherein the capture agent is coupled to at least one of the first surface and the second surface of the substantially non-transparent polymer layer in at least a center portion of the substantially non-transparent polymer layer.

In some embodiments, the microcarrier further comprises (c) one or more columns projecting from the first surface and/or the second surface of the substantially non-transparent polymer layer, wherein the one or more columns comprise a magnetic material. In some embodiments, the one or more columns are between about 1 µm and about 10 µm tall. In some embodiments, the one or more columns are between about 1 µm and about 10 µm in diameter. In some embodiments, the microcarrier further comprises (d) a magnetic layer comprising a magnetic material affixed to the second surface of the substantially non-transparent polymer layer, wherein the magnetic layer does not extend beyond the center portion of the substantially non-transparent polymer layer, and wherein the capture agent is coupled to at least the first surface of the substantially non-transparent polymer layer. In some embodiments, the microcarrier further comprises (e) a second substantially non-transparent polymer layer aligned with the first substantially non-transparent polymer layer, wherein the second substantially non-transparent polymer layer is affixed to the second surface of the first substantially transparent polymer layer and does not extend beyond the outline of the first substantially transparent polymer layer, and wherein the magnetic layer is affixed between the first and the second substantially transparent polymer layers. In some embodiments, the magnetic material comprises nickel. In some embodiments, the microcarrier further comprises an orientation indicator for orienting the analog code of the substantially non-transparent polymer layer. In some embodiments, the orientation indicator comprises an asymmetry of the outline of the substantially non-transparent polymer layer. In some embodiments, the outline of the substantially non-transparent polymer layer comprises a two-dimensional gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 μm and about 10 μm wide. In some embodiments, the plurality of gear teeth comprises one or more gear teeth that are between about 1 μm and about 10 μm tall. In some embodiments, the plurality of gear teeth comprises two or more gear teeth that are spaced between about 1 μm and about 10 μm apart. In some embodiments, the microcarrier is a substantially circular disc. In some embodiments, the center portion of the first substantially non-transparent polymer layer comprises between about 5% and about 90% of the surface area of the first substantially non-transparent polymer layer. In some embodiments, the center portion of the first substantially non-transparent polymer layer comprises about 25% of the surface area of the first substantially non-transparent polymer layer. In some embodiments, the microcarrier is less than about 200 μm in diameter. In some embodiments, the microcarrier is about 60 μm in diameter. In some embodiments, the microcarrier is less than about 50 μm in thickness. In some embodiments, the microcarrier is about 10 μm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the capture agent for capturing the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially non-transparent polymer comprises an epoxy-based polymer. In some embodiments, the substantially non-transparent polymer comprises a black matrix resist.

In another aspect, provided herein is a method of making an encoded microcarrier, comprising: (a) depositing a substantially transparent polymer layer, wherein the substantially transparent polymer layer has a first surface and a second surface, the first and the second surfaces being parallel to each other; (b) depositing a magnetic, substantially non-transparent layer on the first surface of the substantially transparent polymer layer; (c) etching the magnetic, substantially non-transparent layer to remove a portion of the magnetic, substantially non-transparent layer that is deposited over a center portion of the substantially transparent polymer layer; (d) depositing a second substantially transparent polymer layer over the magnetic, substantially non-transparent layer, wherein the second substantially transparent polymer layer has a first surface and a second surface, the first and the second surfaces being parallel to each other, wherein the second surface is affixed to the magnetic, substantially non-transparent layer, and wherein the second substantially transparent polymer layer is aligned with the first substantially transparent polymer layer and has a center portion that is aligned with the center portion of the substantially transparent polymer layer; and (e) depositing a substantially non-transparent polymer layer on the first surface of the second substantially transparent polymer layer, wherein the substantially non-transparent polymer layer encloses the center portions of the first and the second substantially transparent polymer layers, and wherein the substantially non-transparent polymer layer comprises a two-dimensional shape representing an analog code.

In some embodiments, the magnetic, substantially non-transparent layer is etched by wet etching. In some embodiments, the magnetic, substantially non-transparent layer comprises nickel. In some embodiments, the magnetic, substantially non-transparent layer is between about 50 nm and about 10 μm in thickness. In some embodiments, the magnetic, substantially non-transparent layer is less than about 0.1 μm in thickness. In some embodiments, the magnetic, substantially non-transparent layer comprises an asymmetry for orienting the analog code of the substantially non-transparent polymer layer. In some embodiments, the two-dimensional shape of the substantially non-transparent polymer layer is generated by lithography. In some embodiments, the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 μm and about 10 μm wide. In some embodiments, the plurality of gear teeth comprises one or more gear teeth that are between about 1 μm and about 10 μm tall. In some embodiments, the plurality of gear teeth comprises two or more gear teeth that are spaced between about 1 μm and about 10 μm apart. In some embodiments, the method further comprises (f) before step (a), depositing a sacrificial layer on a substrate; (g) creating one or more column-shaped holes in the sacrificial layer using lithography; (h) depositing a third substantially transparent polymer layer in the one or more column-shaped holes in the sacrificial layer, wherein the first substantially transparent polymer layer is deposited in step (a) on top of the third substantially transparent polymer layer and the sacrificial layer; (i) after step (e), depositing using lithography one or more columns comprising the substantially transparent polymer on the first surface of the second substantially transparent polymer layer at a portion not covered by the substantially non-transparent polymer layer; (j) dissolving the sacrificial layer in a solvent; and (k) removing the substrate. In some embodiments, the method further comprises: (f) before step (a), depositing a sacrificial layer on a substrate; (g) as part of step (a), depositing the substantially transparent polymer layer on the sacrificial layer; (h) after step (e), dissolving the sacrificial layer in a solvent; and (i) removing the substrate. In some embodiments, the encoded microcarrier is a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the encoded microcarrier is less than about 200 μm in diameter. In some embodiments, the encoded microcarrier is about 50 μm in diameter. In some embodiments, the encoded microcarrier is less than about 50 μm in thickness. In some embodiments, the encoded microcarrier is about 10 μm in thickness. In some embodiments, the method further comprises: (f) coupling a capture agent for capturing an analyte to at least one of the first surface of the second substantially transparent polymer layer and the second surface of the first substantially transparent polymer layer in at least the center portion. In some embodiments, the substantially transparent polymer of the first or the second substantially transparent polymer layer comprises an epoxide, and coupling the capture agent comprises: (i) reacting the substantially transparent polymer of the first and/or the second substantially transparent polymer layers with a photoacid generator and light to generate a cross-linked polymer, wherein the light is of a wavelength that activates the photoacid generator; and (ii) reacting the epoxide of the cross-linked polymer with a compound comprising an amine and a carboxyl, wherein the amine of the compound reacts with the epoxide to form a compound-coupled, cross-linked polymer; and (iii) reacting the carboxyl of the compound-coupled, cross-linked polymer with the capture agent to couple the capture agent to at least one of the first surface of the second substantially transparent polymer layer and the second surface of the first substantially transparent polymer layer in at least the center portion. In some embodiments, the carboxyl of the compound-coupled, cross-linked polymer reacts with a primary amine of the capture agent. In some embodiments, the substantially transparent polymer of the first and/or the second substantially transparent polymer layers comprise SU-8. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the capture agent for capturing the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment.

In another aspect, provided herein is an encoded microcarrier produced by the method of any of the above embodiments.

In another aspect, provided herein is a method of making an encoded microcarrier, comprising: (a) depositing a sacrificial layer on a substrate; (b) depositing on the sacrificial layer a substantially non-transparent polymer layer having an outline, a first surface, and a second surface, the first and the second surfaces being parallel to each other, wherein the second surface is affixed to the sacrificial layer; (c) shaping by lithography the outline of the substantially non-transparent polymer layer, wherein the outline is shaped into a two-dimensional shape representing an analog code; (d) dissolving the sacrificial polymer layer in a solvent; and (e) removing the substrate. In another aspect, provided herein is a method of making an encoded microcarrier, comprising: (a) depositing a sacrificial layer on a substrate; (b) depositing a magnetic layer comprising a magnetic material on the sacrificial layer; (c) depositing on the magnetic layer a substantially non-transparent polymer layer having an outline, a first surface, and a second surface, the first and the second surfaces being parallel to each other, wherein the second surface is affixed to the magnetic layer; (d) shaping by lithography the outline of the substantially non-transparent polymer layer, wherein the outline is shaped into a two-dimensional shape representing an analog code; (e) dissolving the sacrificial polymer layer in a solvent; and (f) removing the substrate.

In some embodiments, the methods further include (g) after step (b) and before step (c), shaping the magnetic layer by lithography. In some embodiments, the magnetic material comprises nickel. In some embodiments, the microcarrier comprises an orientation indicator for orienting the analog code of the substantially non-transparent polymer layer. In some embodiments, the orientation indicator comprises an asymmetry of the outline of the substantially non-transparent polymer layer. In some embodiments, the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 μm and about 10 μm wide. In some embodiments, the plurality of gear teeth comprises one or more gear teeth that are between about 1 μm and about 10 μm tall. In some embodiments, the plurality of gear teeth comprises two or more gear teeth that are spaced between about 1 μm and about 10 μm apart. In some embodiments, the microcarrier is a substantially circular disc. In some embodiments, the microcarrier is less than about 200 μm in diameter. In some embodiments, the microcarrier is about 60 μm in diameter. In some embodiments, the microcarrier is less than about 30 μm in thickness. In some embodiments, the microcarrier is about 10 μm in thickness. In some embodiments, the method further includes (h) coupling a capture agent for capturing an analyte to at least one of the first surface and the second surface of the substantially non-transparent polymer layer. In some embodiments, the substantially non-transparent polymer of the substantially non-transparent polymer layer comprises an epoxide, and coupling the capture agent comprises: (i) reacting the substantially non-transparent polymer of the substantially non-transparent polymer layer with a photoacid generator and light to generate a cross-linked polymer, wherein the light is of a wavelength that activates the photoacid generator; and (ii) reacting the epoxide of the cross-linked polymer with a compound comprising an amine and a carboxyl, wherein the amine of the compound reacts with the epoxide to form a compound-coupled, cross-linked polymer; and (iii) reacting the carboxyl of the compound-coupled, cross-linked polymer with the capture agent to couple the capture agent to at least one of the first surface of the second substantially transparent polymer layer and the second surface of the first substantially transparent polymer layer in at least the center portion. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the capture agent for capturing the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment.

In another aspect, provided herein is an encoded microcarrier produced by the method of any of the above embodiments.

In another aspect, provided herein is a method for detecting two or more analytes in a solution, comprising: (a) contacting a solution comprising a first analyte and a second analyte with a plurality of microcarriers, wherein the plurality of microcarriers comprises at least: (i) a first microcarrier according to any of the above embodiments that specifically captures the first analyte, wherein the first microcarrier is encoded with a first analog code; and (ii) a second microcarrier according to any of the above embodiments that specifically captures the second analyte, wherein the second microcarrier is encoded with a second analog code, and wherein the second analog code is different from the first analog code; (b) decoding the first analog code and the second analog code using analog shape recognition to identify the first microcarrier and the second microcarrier; and (c) detecting an amount of the first analyte bound to the first microcarrier and an amount of the second analyte bound to the second microcarrier.

In some embodiments, step (b) occurs before step (c). In some embodiments, step (c) occurs before step (b). In some embodiments, step (b) occurs simultaneously with step (c). In some embodiments, decoding the first analog code and the second analog code comprises: (i) illuminating the first and second microcarriers by passing light through the substantially transparent portions of the first and second microcarriers and/or the surrounding solution, wherein the light fails to pass through the substantially non-transparent portions of the first and second microcarriers to generate a first analog-coded light pattern corresponding to the first microcarrier and a second analog-coded light pattern corresponding to the second microcarrier; (ii) imaging the first analog-coded light pattern to generate a first analog-coded image and imaging the second analog-coded light pattern to generate a second analog-coded image; and (iii) using analog shape recognition to match the first analog-coded image with the first analog code and to match the second analog-coded image with the second analog code. In some embodiments, detecting the amount of the first analyte bound to the first microcarrier and the amount of the second analyte bound to the second microcarrier comprises: (i) after step (a), incubating the first and the second microcarriers with a detection agent, wherein the detection agent binds the first analyte captured by the first microcarrier and the second analyte captured by the second microcarrier; and (ii) measuring the amount of detection agent bound to the first and the second microcarriers. In some embodiments, the detection agent is a fluorescent detection agent, and the amount of detection agent bound to the first and the second microcarriers is measured by fluorescence microscopy. In some embodiments, the detection agent is a luminescent detection agent, and the amount of detection agent bound to the first and the second microcarriers is measured by luminescence microscopy. In some embodiments, the solution comprises a biological sample. In some embodiments, the biological sample is selected from the group consisting of blood, urine, sputum, bile, cerebrospinal fluid, interstitial fluid of skin or adipose tissue, saliva, tears, bronchial-alveolar lavage, oro-pharyngeal secretions, intestinal fluids, cervico-vaginal or uterine secretions, and seminal fluid.

In another aspect, provided herein is a kit or article of manufacture comprising a plurality of microcarriers, wherein the plurality of microcarriers comprises at least: (a) a first microcarrier according to any of the above embodiments that specifically captures a first analyte, wherein the first microcarrier is encoded with a first analog code; and (b) a second microcarrier according to any of the above embodiments that specifically captures a second analyte, wherein the second microcarrier is encoded with a second analog code, and wherein the second analog code is different from the first analog code.

In some embodiments, the kit or article of manufacture further comprises a detection agent for detecting an amount of the first analyte bound to the first microcarrier and an amount of the second analyte bound to the second microcarrier. In some embodiments, the kit or article of manufacture further comprises instructions for using the kit to detect the first analyte and the second analyte.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIGS. 1C & 1D show an exemplary assay for analyte detection using an exemplary microcarrier.

FIGS. 2A & 2B show two views of an exemplary microcarrier.

FIGS. 5A & 5B show two views of an exemplary microcarrier.

FIGS. 6A & 6B show two views of an exemplary microcarrier.

FIGS. 13A-13C show a method for producing an exemplary microcarrier.

DETAILED DESCRIPTION

Figure 1A:
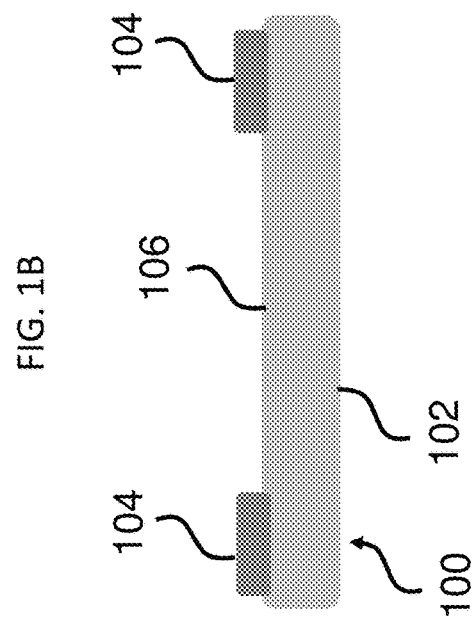
FIGS. 1A & 1B show two views of an exemplary microcarrier.

In one aspect, provided herein are encoded microcarriers for analyte detection in multiplex assays. In some embodiments, the microcarriers include (a) a substantially transparent polymer layer having a first surface and a second surface, the first and the second surfaces being parallel to each other; (b) a substantially non-transparent polymer layer, where the substantially non-transparent polymer layer is affixed to the first surface of the substantially transparent polymer layer and encloses a center portion of the substantially transparent polymer layer, and where the substantially non-transparent polymer layer comprises a two-dimensional shape representing an analog code; and (c) a capture agent for capturing an analyte, where the capture agent is coupled to at least one of the first surface and the second surface of the substantially transparent polymer layer in at least the center portion of the substantially transparent polymer layer. In other embodiments, the microcarriers include (a) a substantially non-transparent polymer layer having a first surface and a second surface, the first and the second surfaces being parallel to each other, wherein an outline of the substantially non-transparent polymer layer comprises a two-dimensional shape that represents an analog code; and (b) a capture agent for capturing an analyte, wherein the capture agent is coupled to at least one of the first surface and the second surface of the substantially non-transparent polymer layer in at least a center portion of the substantially non-transparent polymer layer.

In another aspect, provided herein are methods of making encoded microcarriers. In some embodiments, the methods include (a) depositing a substantially transparent polymer layer, wherein the substantially transparent polymer layer has a first surface and a second surface, the first and the second surfaces being parallel to each other; (b) depositing a magnetic, substantially non-transparent layer on the first surface of the substantially transparent polymer layer; (c) etching the magnetic, substantially non-transparent layer to remove a portion of the magnetic, substantially non-transparent layer that is deposited over a center portion of the substantially transparent polymer layer; (d) depositing a second substantially transparent polymer layer over the magnetic, substantially non-transparent layer, where the second substantially transparent polymer layer has a first surface and a second surface, the first and the second surfaces being parallel to each other, where the second surface is affixed to the magnetic, substantially non-transparent layer, and where the second substantially transparent polymer layer is aligned with the first substantially transparent polymer layer and has a center portion that is aligned with the center portion of the substantially transparent polymer layer; and (e) depositing a substantially non-transparent polymer layer on the first surface of the second substantially transparent polymer layer, where the substantially non-transparent polymer layer encloses the center portions of the first and the second substantially transparent polymer layers, and where the substantially non-transparent polymer layer comprises a two-dimensional shape representing an analog code. In other embodiments, the methods include (a) depositing a sacrificial layer on a substrate; (b) depositing on the sacrificial layer a substantially non-transparent polymer layer having an outline, a first surface, and a second surface, the first and the second surfaces being parallel to each other, where the second surface is affixed to the sacrificial layer; (c) shaping by lithography the outline of the substantially non-transparent polymer layer, where the outline is shaped into a two-dimensional shape representing an analog code; (d) dissolving the sacrificial polymer layer in a solvent; and (e) removing the substrate. In other embodiments, the methods include (a) depositing a sacrificial layer on a substrate; (b) depositing a magnetic layer comprising a magnetic material on the sacrificial layer; (c) depositing on the magnetic layer a substantially non-transparent polymer layer having an outline, a first surface, and a second surface, the first and the second surfaces being parallel to each other, wherein the second surface is affixed to the magnetic layer; (d) shaping by lithography the outline of the substantially non-transparent polymer layer, where the outline is shaped into a two-dimensional shape representing an analog code; (d) dissolving the sacrificial polymer layer in a solvent; and (e) removing the substrate. Further provided herein are encoded microcarriers produced by the methods disclosed herein.

In still another aspect, provided herein are methods for detecting two or more analytes in a solution by (a) contacting a solution comprising a first analyte and a second analyte with a plurality of microcarriers, where the plurality of microcarriers includes at least: (i) a first microcarrier of the present disclosure that specifically captures the first analyte, where the first microcarrier is encoded with a first analog code; and (ii) a second microcarrier of the present disclosure that specifically captures the second analyte, where the second microcarrier is encoded with a second analog code, and where the second analog code is different from the first analog code; (b) decoding the first analog code and the second analog code using analog shape recognition to identify the first microcarrier and the second microcarrier; and (c) detecting an amount of the first analyte bound to the first microcarrier and an amount of the second analyte bound to the second microcarrier.

In yet another aspect, provided herein are kits or articles of manufacture for conducting a multiplex assay including a plurality of microcarriers. The plurality of microcarriers includes at least (a) a first microcarrier of the present disclosure that specifically captures a first analyte, where the first microcarrier is encoded with a first analog code; and (b) a second microcarrier of the present disclosure that specifically captures a second analyte, where the second microcarrier is encoded with a second analog code, and where the second analog code is different from the first analog code.

I. General Techniques

The practice of the techniques described herein will employ, unless otherwise indicated, conventional techniques in polymer technology, microfabrication, micro-electro-mechanical systems (MEMS) fabrication, photolithography, microfluidics, organic chemistry, biochemistry, oligonucleotide synthesis and modification, bioconjugate chemistry, nucleic acid hybridization, molecular biology, microbiology, genetics, recombinant DNA, and related fields as are within the skill of the art. The techniques are described in the references cited herein and are fully explained in the literature.

For molecular biology and recombinant DNA techniques, see, for example, (Maniatis, T. et al. (1982), *Molecular Cloning: A Laboratory Manual*, Cold Spring Harbor; Ausubel, F. M. (1987), *Current Protocols in Molecular Biology*, Greene Pub. Associates and Wiley-Interscience; Ausubel, F. M. (1989), *Short Protocols in Molecular Biology: A Compendium of Methods from Current Protocols in Molecular Biology*, Greene Pub. Associates and Wiley-Interscience; Sambrook, J. et al. (1989), *Molecular Cloning: A Laboratory Manual*, Cold Spring Harbor; Innis, M. A. (1990), *PCR Protocols: A Guide to Methods and Applications*, Academic Press; Ausubel, F. M. (1992), *Short Protocols in Molecular Biology: A Compendium of Methods from Current Protocols in Molecular Biology*, Greene Pub. Associates; Ausubel, F. M. (1995), *Short Protocols in Molecular Biology: A Compendium of Methods from Current Protocols in Molecular Biology*, Greene Pub. Associates; Innis, M. A. et al. (1995), *PCR Strategies, Academic Press*; Ausubel, F. M. (1999), *Short Protocols in Molecular Biology: A Compendium of Methods from Current Protocols in Molecular Biology*, Wiley, and annual updates.

For DNA synthesis techniques and nucleic acids chemistry, see for example, Gait, M. J. (1990), *Oligonucleotide Synthesis: A Practical Approach*, IRL Press; Eckstein, F. (1991), *Oligonucleotides and Analogues: A Practical Approach*, IRL Press; Adams, R. L. et al. (1992), *The Biochemistry of the Nucleic Acids*, Chapman & Hall; Shabarova, Z. et al. (1994), *Advanced Organic Chemistry of Nucleic Acids*, Weinheim; Blackburn, G. M. et al. (1996), *Nucleic Acids in Chemistry and Biology*, Oxford University Press; Hermanson, G. T. (1996), *Bioconjugate Techniques*, Academic Press).

For microfabrication, see for example, (Campbell, S. A. (1996), *The Science and Engineering of Microelectronic Fabrication*, Oxford University Press; Zaut, P. V. (1996), *Microarray Fabrication: a Practical Guide to Semiconductor Processing*, Semiconductor Services; Madou, M. J. (1997), *Fundamentals of Microfabrication*, CRC Press; Rai-Choudhury, P. (1997). Handbook of Microlithography, Micromachining, & Microfabrication: Microlithography).

II. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

The term "microcarrier" as used herein may refer to a physical substrate onto which a capture agent may be coupled. A microcarrier of the present disclosure may take any suitable geometric form or shape. In some embodiments, the microcarrier may be disc-shaped. Typically the form or shape of a microcarrier will include at least one dimension on the order of $10^{-4}$ to $10^{-7}$ m (hence the prefix "micro").

The term "polymer" as used herein may refer to any macromolecular structure comprising repeated monomers. A polymer may be natural (e.g., found in nature) or synthetic (e.g., man-made, such as a polymer composed of non-natural monomer(s) and/or polymerized in a configuration or combination not found in nature).

The terms "substantially transparent" and "substantially non-transparent" as used herein may refer to the ability of light (e.g., of a particular wavelength, such as infrared, visible, UV, and so forth) to pass through a substrate, such as a polymer layer. A substantially transparent polymer may refer to one that is transparent, translucent, and/or pervious to light, whereas a substantially non-transparent polymer may refer to one that reflects and/or absorbs light. It is to be appreciated that whether a material is substantially transparent or substantially non-transparent may depend upon the wavelength and/or intensity of light illuminating the material, as well as the means detecting the light traveling through the material (or a decrease or absence thereof). In some embodiments, a substantially non-transparent material causes a perceptible decrease in transmitted light as compared to the surrounding material or image field, e.g., as imaged by light microscopy (e.g., bright field, dark field, phase contrast, differential interference contrast (DIC), Nomarski interference contrast (NIC), Nomarski, Hoffman modulation contrast (HMC), or fluorescence microscopy). In some embodiments, a substantially transparent material allows a perceptible amount of transmitted light to pass through the material, e.g., as imaged by light microscopy (e.g., bright field, dark field, phase contrast, differential interference contrast (DIC), Nomarski interference contrast (NIC), Nomarski, Hoffman modulation contrast (HMC), or fluorescence microscopy).

The term "analog code" as used herein may refer to any code in which the encoded information is represented in a non-quantized and/or non-discrete manner, e.g., as opposed to a digital code. For example, a digital code is sampled at discrete positions for a limited set of values (e.g., 0/1 type values), whereas an analog code may be sampled at a greater range of positions (or as a continuous whole) and/or may contain a wider set of values (e.g., shapes). In some embodiments, an analog code may be read or decoded using one or more analog shape recognition techniques.

The term "capture agent" as used herein is a broad term and is used in its ordinary sense to refer to any compound or substance capable of specifically recognizing an analyte of interest. In some embodiments, specific recognition may refer to specific binding. Non-limiting examples of capture agents include, for example, a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment.

"Analyte," as used herein, is a broad term and is used in its ordinary sense as a substance the presence, absence, or quantity of which is to be determined, including, without limitation, to refer to a substance or chemical constituent in a sample such as a biological sample or cell or population of cells that can be analyzed. An analyte can be a substance for which a naturally occurring binding member exists, or for which a binding member can be prepared. Non-limiting examples of analytes include, for example, antibodies, antibody fragments, antigens, polynucleotides (such as a DNA molecule, DNA-analog-molecule, RNA-molecule, or RNA-analog-molecule), polypeptides, proteins, enzymes, lipids, phospholipids, carbohydrate moieties, polysaccharides, small molecules, organelles, hormones, cytokines, growth factors, steroids, vitamins, toxins, drugs, and metabolites of the above substances, as well as cells, bacteria, viruses, fungi, algae, fungal spores and the like.

The term "antibody" is used in the broadest sense and includes monoclonal antibodies (including full length antibodies which have an immunoglobulin Fc region), polyclonal antibodies, multispecific antibodies (e.g., bispecific antibodies, diabodies, and single-chain molecules), as well as antibody fragments (e.g., Fab, F(ab')$_2$, and Fv).

As used herein, "sample" refers to a composition containing a material, such as a molecule, to be detected. In one embodiment, the sample is a "biological sample" (i.e., any material obtained from a living source (e.g. human, animal, plant, bacteria, fungi, protist, virus)). The biological sample can be in any form, including solid materials (e.g. tissue, cell pellets and biopsies) and biological fluids (e.g. urine, blood, saliva, lymph, tears, sweat, prostatic fluid, seminal fluid, semen, bile, mucus, amniotic fluid and mouth wash (containing buccal cells)). Solid materials typically are mixed with a fluid. Sample can also refer to an environmental sample such as water, air, soil, or any other environmental source.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

III. Encoded Microcarriers

Provided herein are encoded microcarriers suitable for analyte detection, e.g., multiplex analyte detection. Multiple configurations for encoded microcarriers are contemplated, described, and exemplified herein.

In some aspects, provided herein are encoded microcarriers that comprise: a substantially transparent polymer layer having a first surface and a second surface, the first and the second surfaces being parallel to each other; a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code; and a capture agent for capturing an analyte, wherein the capture agent is coupled to at least one of the first surface and the second surface of the substantially transparent polymer layer in at least the center portion of the substantially transparent polymer layer. Thus, the microcarrier contains at least two layers: one of which is substantially transparent, and the other of which is a substantially non-transparent, two-dimensional shape that represents an analog code. Advantageously, these microcarriers may employ a variety of two-dimensional shapes while still retaining a uniform overall form (e.g., the perimeter of the substantially transparent polymer layer) for uniformity of aspects including, for example, overall dimensions, physical properties, and/or behavior in solution. Examples of this type of microcarrier and aspects thereof are illustrated in FIGS. 1A-5B.

In some embodiments, the microcarrier further includes a magnetic, substantially non-transparent layer affixed to a surface of the substantially transparent polymer layer that encloses the center portion of the substantially transparent polymer layer. In some embodiments, the magnetic, substantially non-transparent layer is between the substantially non-transparent polymer layer and the center portion of the substantially transparent polymer layer.

In some embodiments, the microcarrier further includes a second substantially transparent polymer layer aligned with and affixed to the first substantially transparent polymer layer. In some embodiments, the first and second substantially transparent polymer layers each have a center portion, and the center portions of both the first and second substantially transparent polymer layers are aligned. In some embodiments, the microcarrier further includes a magnetic, substantially non-transparent layer that encloses the center portions of both the first and second substantially transparent polymer layers. In some embodiments, the magnetic, substantially non-transparent layer is affixed between the first and second substantially transparent polymer layers. In some embodiments, the magnetic, substantially non-transparent layer is between the substantially non-transparent polymer layer and the center portions of both the first and second substantially transparent polymer layers.

In some embodiments, the magnetic, substantially non-transparent layer is between about 50 nm and about 10 µm in thickness. In some embodiments, the thickness of the magnetic, substantially non-transparent layer is less than about any of the following thicknesses (in nm): 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100. In some embodiments, the thickness of the magnetic, substantially non-transparent layer is greater than about any of the following thicknesses (in nm): 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500. That is, the thickness of the magnetic, substantially non-transparent layer may be any of a range of thicknesses (in nm) having an upper limit of 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100 and an independently selected lower limit of 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500, wherein the lower limit is less than the upper limit.

In some embodiments, the magnetic, substantially non-transparent layer is about 0.1 µm in thickness. In some embodiments, the magnetic, substantially non-transparent layer is about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1 µm, about 1.5 µm, about 2 µm, about 2.5 µm, about 3 µm, about 3.5 µm, about 4 µm, about 4.5 µm, about 5 µm, about 5.5 µm, about 6 µm, about 6.5 µm, about 7 µm, about 7.5 µm, about 8 µm, about 8.5 µm, about 9 µm, about 9.5 µm, or about 10 µm in thickness. In some embodiments, the thickness of the magnetic, substantially non-transparent layer is about 0.01 µm, about 0.02 µm, about 0.03 µm, about 0.04 µm, about 0.05 µm, about 0.06 µm, about 0.07 µm, about 0.08 µm, about 0.09 µm, about 0.1 µm, about 0.11 µm, about 0.12 µm, about 0.13 µm, about 0.14 µm, about 0.15 µm, about 0.16 µm, about 0.17 µm, about 0.18 µm, about 0.19 µm, about 0.20 µm, about 0.25 µm, about 0.30 µm, about 0.35 µm, about 0.40 µm, about 0.45 µm, or about 0.50 µm.

In some embodiments, the microcarrier further includes an orientation indicator for orienting the analog code of the substantially non-transparent polymer layer. Any feature of the microcarrier that is visible and/or detectable by imaging (e.g., a form of microscopic or other imaging described herein) and/or by image recognition software may serve as an orientation indicator. An orientation indicator may serve as a point of reference, e.g., for an image recognition algorithm, to orient the image of an analog code in a uniform orientation (i.e., the shape of the substantially non-transparent polymer layer). Advantageously, this simplifies image recognition, as the algorithm would only need to compare the image of a particular analog code against a library of analog codes in the same orientation, and not against a library including all analog codes in all possible orientations. In some embodiments, the orientation indicator may be independent of the substantially non-transparent polymer layer. For example, it may be formed as a part of a magnetic layer and/or substantially transparent polymer layer. In other embodiments, the orientation indicator may be formed as part of the substantially non-transparent polymer layer. In some embodiments, the orientation indicator comprises an asymmetry of the magnetic, substantially non-transparent layer (e.g., as illustrated by gap 210 in FIG. 2A).

In some embodiments, the microcarrier further includes one or more columns projecting from a surface of the microcarrier (e.g., the top and/or bottom surface of the microcarrier). As used herein, a "column" may refer to any geometric shape that projects from the microcarrier surface and does not necessarily denote any regularity in dimensions, nor any cylindrical character. For example, the outer surface of a column may or may not be parallel with the microcarrier surface. Examples of columnar shapes that may project from a microcarrier include without limitation a rectangular prism, a triangle, a pyramid, a cube, a cylinder, a sphere or half-sphere, a cone, and so forth. In some embodiments, the one or more columns are not within a center portion of the first and/or the second substantially transparent polymer layer. In some embodiments, the one or more columns may project from an outside-facing surface (e.g., a surface not affixed to another layer) of one or more of the first and the second substantially transparent polymer layers. It is to be noted that any descriptions of microcarrier thickness herein do not include the one or more columns in the stated dimensions. That is to say, microcarrier thickness as described herein is independent of any optional columns projecting therefrom.

In some embodiments, the one or more columns are between about 1 µm and about 10 µm tall. In some embodiments, the one or more columns are about 1 µm tall, about 1.5 µm tall, about 2 µm tall, about 2.5 µm tall, about 3 µm tall, about 3.5 µm tall, about 4 µm tall, about 4.5 µm tall, about 5 µm tall, about 5.5 µm tall, about 6 µm tall, about 6.5 µm tall, about 7 µm tall, about 7.5 µm tall, about 8 µm tall, about 8.5 µm tall, about 9 µm tall, about 9.5 µm tall, or about 10 µm tall. In some embodiments, the one or more columns are less than about any of the following heights (in µm): 10, 9.5, 9, 8.5, 8, 7.5, 7, 6.5, 6, 5.5, 5, 4.5, 4, 3.5, 3, 2.5, 2, or 1.5. In some embodiments, the one or more columns are greater than about any of the following heights (in µm): 1, 1.5, 2, 2.5, 3, 3.5, 4, 4.5, 5, 5.5, 6, 6.5, 7, 7.5, 8, 8.5, 9, or 9.5. That is, the one or more columns can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the one or more columns may be cylindrical in shape. In some embodiments, the one or more columns have a diameter between about 1 µm and about 10 µm. In some embodiments, the one or more columns have a diameter of about 1 µm, about 1.5 µm, about 2 µm, about 2.5 µm, about 3 µm, about 3.5 µm, about 4 µm, about 4.5 µm, about 5 µm, about 5.5 µm, about 6 µm, about 6.5 µm, about 7 µm, about 7.5 µm, about 8 µm, about 8.5 µm, about 9 µm, about 9.5 µm, or about 10 µm. In some embodiments, the one or more columns have a diameter less than about any of the following lengths (in µm): 10, 9.5, 9, 8.5, 8, 7.5, 7, 6.5, 6, 5.5, 5, 4.5, 4, 3.5, 3, 2.5, 2, or 1.5. In some embodiments, the one or more columns have a diameter greater than about any of the following lengths (in µm): 1, 1.5, 2, 2.5, 3, 3.5, 4, 4.5, 5, 5.5, 6, 6.5, 7, 7.5, 8, 8.5, 9, or 9.5. That is, the one or more columns can have any of a range of diameters having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. In other embodiments, the one or more columns may have roughly the same width as any diameter described supra, or a range of widths roughly the same as any range of diameters described supra, but the one or more columns may adopt the shape of an elliptical cylinder, parabolic cylinder, hyperbolic cylinder, or any other cylindrical or polyhedral shape described herein or known in the art.

In other aspects, provided herein are encoded microcarriers that comprise: a substantially non-transparent polymer layer having a first surface and a second surface, the first and the second surfaces being parallel to each other, wherein an outline of the substantially non-transparent polymer layer comprises a two-dimensional shape that represents an analog code; and a capture agent for capturing an analyte, wherein the capture agent is coupled to at least one of the first surface and the second surface of the substantially non-transparent polymer layer in at least a center portion of the substantially non-transparent polymer layer. Thus, the microcarrier is encoded by the shape (e.g., outline) of the microcarrier itself: a two-dimensional shape that represents an analog code. Advantageously, these microcarriers may be manufactured efficiently and with high precision, allowing for highly accurate decoding and cost-efficient production. Examples of this type of microcarrier and aspects thereof are illustrated in FIGS. 6A-9C.

In some embodiments, the microcarrier further includes one or more columns projecting from a surface of the substantially non-transparent polymer layer. As described in greater detail supra, a "column" may refer to any geometric shape that projects from the microcarrier surface and does not necessarily denote any regularity in columnar dimension(s). Any of the exemplary columnar shapes described above may be used.

In some embodiments, the one or more columns are between about 1 µm and about 10 µm tall. In some embodiments, the one or more columns are about 1 µm tall, about 1.5 µm tall, about 2 µm tall, about 2.5 µm tall, about 3 µm tall, about 3.5 µm tall, about 4 µm tall, about 4.5 µm tall, about 5 µm tall, about 5.5 µm tall, about 6 µm tall, about 6.5 µm tall, about 7 µm tall, about 7.5 µm tall, about 8 µm tall, about 8.5 µm tall, about 9 µm tall, about 9.5 µm tall, or about 10 µm tall. In some embodiments, the one or more columns are less than about any of the following heights (in µm): 10, 9.5, 9, 8.5, 8, 7.5, 7, 6.5, 6, 5.5, 5, 4.5, 4, 3.5, 3, 2.5, 2, or 1.5. In some embodiments, the one or more columns are greater than about any of the following heights (in µm): 1, 1.5, 2, 2.5, 3, 3.5, 4, 4.5, 5, 5.5, 6, 6.5, 7, 7.5, 8, 8.5, 9, or 9.5. That is, the one or more columns can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the one or more columns may be cylindrical in shape. In some embodiments, the one or more columns have a diameter between about 1 µm and about 10 µm. In some embodiments, the one or more columns have a diameter of about 1 µm, about 1.5 µm, about 2 µm, about 2.5 µm, about 3 µm, about 3.5 µm, about 4 µm, about 4.5 µm, about 5 µm, about 5.5 µm, about 6 µm, about 6.5 µm, about 7 µm, about 7.5 µm, about 8 µm, about 8.5 µm, about 9 µm, about 9.5 µm, or about 10 µm. In some embodiments, the one or more columns have a diameter less than about any of the following lengths (in μm): 10, 9.5, 9, 8.5, 8, 7.5, 7, 6.5, 6, 5.5, 5, 4.5, 4, 3.5, 3, 2.5, 2, or 1.5. In some embodiments, the one or more columns have a diameter greater than about any of the following lengths (in μm): 1, 1.5, 2, 2.5, 3, 3.5, 4, 4.5, 5, 5.5, 6, 6.5, 7, 7.5, 8, 8.5, 9, or 9.5. That is, the one or more columns can have any of a range of diameters having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. In other embodiments, the one or more columns may have roughly the same width as any diameter described supra, or a range of widths roughly the same as any range of diameters described supra, but the one or more columns may adopt the shape of an elliptical cylinder, parabolic cylinder, hyperbolic cylinder, or any other cylindrical or polyhedral shape described herein or known in the art.

In some embodiments, the microcarrier further includes a magnetic layer comprising a magnetic material affixed to a surface of the substantially non-transparent polymer layer. In some embodiments, the magnetic layer does not extend beyond the two-dimensional shape of the substantially non-transparent polymer layer. That is to say, if the outline of the substantially non-transparent polymer layer were to be imaged, the resulting image would not be altered by the presence or absence of the magnetic layer. In some embodiments, the magnetic layer may include the one or more columns described above. That is, the one or more columns described above may be made of a magnetic material described herein.

In some embodiments, the microcarrier further includes an orientation indicator for orienting the analog code of the substantially non-transparent polymer layer. Any feature of the microcarrier that is visible and/or detectable by imaging (e.g., a form of microscopic or other imaging described herein) and/or by image recognition software may serve as an orientation indicator. An orientation indicator may serve as a point of reference, e.g., for an image recognition algorithm, to orient the image of an analog code in a uniform orientation (i.e., the shape of the substantially non-transparent polymer layer). Advantageously, this simplifies image recognition, as the algorithm would only need to compare the image of a particular analog code against a library of analog codes in the same orientation, and not against a library including all analog codes in all possible orientations. In some embodiments, the orientation indicator comprises an asymmetry of the outline of the substantially non-transparent polymer layer. For example, the orientation indicator may comprise a visible feature, such as an asymmetry, of the outline of the microcarrier (e.g., as illustrated by start positions 804 and 904 in FIGS. 8A and 9A).

Any of the microcarriers described herein may include one or more of the features, elements, or aspects described below. In addition, one or more of the features, elements, or aspects described below may adopt different characteristics depending on the embodiment of the microcarrier, e.g., as described above.

In some embodiments, a substantially transparent polymer of the present disclosure comprises an epoxy-based polymer. Suitable epoxy-based polymers for fabrication of the compositions described herein include, but are not limited to, the EPON™ family of epoxy resins provided by Hexion Specialty Chemicals, Inc. (Columbus, Ohio) and any number of epoxy resins provided by The Dow Chemical Company (Midland, Mich.). Many examples of suitable polymers are commonly known in the art, including without limitation SU-8, EPON 1002F, EPON 165/154, and a poly (methyl methacrylate)/poly(acrylic acid) block copolymer (PMMA-co-PAA). For additional polymers, see, for example, Warad, IC Packaging: Package Construction Analysis in Ultra Small IC Packaging, LAP LAMBERT Academic Publishing (2010); *The Electronic Packaging Handbook*, CRC Press (Blackwell, ed.), (2000); and Pecht et al., *Electronic Packaging Materials and Their Properties*, CCR Press, 1$^{st}$ ed., (1998). These types of materials have the advantage of not swelling in aqueous environments which ensures that uniform microcarrier size and shape are maintained within the population of microcarriers. In some embodiments, the substantially transparent polymer is a photoresist polymer. In some embodiments, the epoxy-based polymer is an epoxy-based, negative-tone, near-UV photoresist. In some embodiments, the epoxy-based polymer is SU-8.

In some embodiments, the substantially non-transparent polymer is a polymer described herein (e.g., SU-8) mixed with one or more non-transparent or colored dye(s). In other embodiments, the substantially non-transparent polymer is a black matrix resist. Any black matrix resist known in the art may be used; see, e.g., U.S. Pat. No. 8,610,848 for exemplary black matrix resists and methods related thereto. In some embodiments, the black matrix resist may be a photoresist colored with a black pigment, e.g., as patterned on the color filter of an LCD as part of a black matrix. Black matrix resists may include without limitation those sold by Toppan Printing Co. (Tokyo), Tokyo OHKA Kogyo (Kawasaki), and Daxin Materials Corp. (Taichung City, Taiwan).

In some embodiments, reference may be made to a center portion of one or more polymer layers. A center portion of the present disclosure may take any shape. In some embodiments, the shape of the center portion may reflect or correspond to the shape (e.g., outline) of the corresponding polymer layer. In other embodiments, the shape of the center portion may be independent of the shape (e.g., outline) of the corresponding polymer layer. For example, a center portion of a circular microcarrier surface may be circular in some embodiments and square in other embodiments. A center portion of a square microcarrier surface may be square in some embodiments and circular in other embodiments.

In some embodiments, a center portion of a polymer layer of the present disclosure is about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, or about 90% of the surface area of the polymer layer. In some embodiments, a center portion of a polymer layer of the present disclosure is less than about any of the following fractions of the substantially transparent polymer layer (in %): 90, 85, 80, 75, 70, 65, 60, 55, 50, 45, 40, 35, 30, 25, 20, 15, 10, or 7. In some embodiments, a center portion of a polymer layer of the present disclosure is greater than about any of the following fractions of the substantially transparent polymer layer (in %): 5, 7, 10, 15, 20, 25, 30, 35, 40, 45, 50, 55, 60, 65, 70, 75, 80, or 85. That is, the fraction of the polymer layer surface area included in the center portion may be any of a range of percentages having an upper limit of 90, 85, 80, 75, 70, 65, 60, 55, 50, 45, 40, 35, 30, 25, 20, 15, 10, or 7 and an independently selected lower limit of 5, 7, 10, 15, 20, 25, 30, 35, 40, 45, 50, 55, 60, 65, 70, 75, 80, or 85, wherein the lower limit is less than the upper limit. In some embodiments, the center portion of a polymer layer comprises about 25% of the surface area of the polymer layer. In some embodiments, a center portion of a microcarrier surface includes the entire surface minus an outline portion of the microcarrier.

As described above, a microcarrier of the present disclosure may further include a magnetic layer, which may adopt a variety of shapes as described herein. In some embodiments, the magnetic layer may be a substantially non-transparent layer. In some embodiments, the magnetic layer may comprise a magnetic material. A magnetic layer of the present disclosure may be made of any suitable magnetic material, such as a material with paramagnetic, ferromagnetic, or ferrimagnetic properties. Examples of magnetic materials include without limitation iron, nickel, cobalt, and some rare earth metals (e.g., gadolinium, dysprosium, neodymium, and so forth), as well as alloys thereof. In some embodiments, the magnetic material comprises nickel, including without limitation elemental nickel and magnetic nickel alloys such as alnico and permalloy. The inclusion of a magnetic layer in a microcarrier of the present disclosure may be advantageous, e.g., in facilitating magnetic separation, which may be useful for washing, collecting, and otherwise manipulating one or more microcarriers.

As described above, in some embodiments, the magnetic layer may be affixed to a surface of the substantially transparent polymer layer and enclose a center portion of the substantially transparent polymer layer. In other embodiments, as described above, the magnetic layer may include one or more columns; i.e., the one or more columns described above may be made of a magnetic material described herein.

In some embodiments, a microcarrier of the present disclosure may be encoded with a substantially non-transparent layer that constitutes a two-dimensional shape. For example, as described above, the two-dimensional shape may constitute the shape of a substantially non-transparent layer that contrasts with a substantially transparent layer of the microcarrier, or it may constitute the shape of the microcarrier itself (e.g., the perimeter). Any two-dimensional shape that can encompass a plurality of resolvable and distinctive varieties may be used. In some embodiments, the two-dimensional shape comprises one or more of linear, circular, elliptical, rectangular, quadrilateral, or higher polygonal aspects, elements, and/or shapes.

In some embodiments, the two-dimensional shape of the substantially non-transparent polymer layer comprises a gear shape. A gear shape as used herein may refer to a plurality of shapes (e.g., gear teeth) arrayed on the perimeter of a substantially round, elliptical, or circular body, where at least two of the shapes of the plurality are spatially separated. In some embodiments, the gear shape comprises a plurality of gear teeth. In some embodiments, the analog code is represented by one or more aspects selected from the height of one or more gear teeth of the plurality, the width of one or more gear teeth of the plurality, the number of gear teeth in the plurality, and the arrangement of one or more gear teeth within the plurality. Advantageously, a gear shape encompasses multiple aspects, including the height of gear teeth, the width of gear teeth, the number of gear teeth, and the arrangement of gear teeth, that may be varied in order to generate a large diversity of potential unique two-dimensional shapes. It is to be appreciated, however, that since the gear shapes of the present disclosure are used for encoding and are not required to physically intermesh with another gear (e.g., as with mechanical gears that transmit torque), gear teeth of the present disclosure are not constrained by the need for identical or intermeshing shapes, either within one gear shape or between multiple gear shapes. As such, the variety of shapes that may be considered a gear tooth of the present disclosure is significantly greater than with a mechanical gear.

In some embodiments, the plurality of gear teeth comprises one or more gear teeth that are between about 1 μm and about 10 μm wide. In some embodiments, the plurality of gear teeth comprises one or more gear teeth that are about 1 μm wide, about 1.5 μm wide, about 2 μm wide, about 2.5 μm wide, about 3 μm wide, about 3.5 μm wide, about 4 μm wide, about 4.5 μm wide, about 5 μm wide, about 5.5 μm wide, about 6 μm wide, about 6.5 μm wide, about 7 μm wide, about 7.5 μm wide, about 8 μm wide, about 8.5 μm wide, about 9 μm wide, about 9.5 μm wide, or about 10 μm wide. In some embodiments, the plurality of gear teeth comprises one or more gear teeth that are less than about any of the following widths (in μm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are greater than about any of the following widths (in μm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be any of a range of widths having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the plurality of gear teeth comprises one or more gear teeth that are between about 1 μm and about 10 μm tall. In some embodiments, the plurality of gear teeth comprises one or more gear teeth that are about 1 μm tall, about 1.5 μm tall, about 2 μm tall, about 2.5 μm tall, about 3 μm tall, about 3.5 μm tall, about 4 μm tall, about 4.5 μm tall, about 5 μm tall, about 5.5 μm tall, about 6 μm tall, about 6.5 μm tall, about 7 μm tall, about 7.5 μm tall, about 8 μm tall, about 8.5 μm tall, about 9 μm tall, about 9.5 μm tall, or about 10 μm tall. In some embodiments, the plurality of gear teeth comprises one or more gear teeth that are less than about any of the following heights (in μm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are greater than about any of the following heights (in μm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. It is to be appreciated that a gear tooth may have different measurable heights, depending on the point of reference, if the adjacent perimeter segments from which the gear tooth extends are uneven (see, e.g., gear tooth 602 in FIG. 6C, which may be 4 or 6.5 μm tall, depending on the point of reference).

In some embodiments, the plurality of gear teeth comprises one or more gear teeth that are spaced between about 1 μm and about 10 μm apart. In some embodiments, the plurality of gear teeth comprises one or more gear teeth that are spaced about 1 μm apart, about 1.5 μm apart, about 2 μm apart, about 2.5 μm apart, about 3 μm apart, about 3.5 μm apart, about 4 μm apart, about 4.5 μm apart, about 5 μm apart, about 5.5 μm apart, about 6 μm apart, about 6.5 μm apart, about 7 μm apart, about 7.5 μm apart, about 8 μm apart, about 8.5 μm apart, about 9 μm apart, about 9.5 μm apart, or about 10 μm apart. In some embodiments, the plurality of gear teeth comprises one or more gear teeth that are spaced less than about any of the following widths (in μm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are spaced greater than about any of the following widths apart (in μm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be spaced any of a range of widths apart having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, a microcarrier of the present disclosure is a substantially circular disc. As used herein, a substantially circular shape may refer to any shape having a roughly identical distance between all of the points of the shape's perimeter and the shape's geometric center. In some embodiments, a shape is considered to be substantially circular if the variation among any of the potential radii connecting the geometric center and a given point on the perimeter exhibit 10% or lesser variation in length. As used herein, a substantially circular disc may refer to any substantially circular shape wherein the thickness of the shape is significantly less than its diameter. For example, in some embodiments, the thickness of a substantially circular disc may be less than about 50%, less than about 40%, less than about 30%, less than about 20%, less than about 15%, less than about 10%, or less than about 5% of its diameter. In certain embodiments, the thickness of the substantially circular disc may about 20% of its diameter. It is to be appreciated that the microcarriers of the present disclosure whose outline is a gear shape may also be considered substantially circular discs; for example, the shape of the microcarrier excluding the one or more gear teeth may comprise a substantially circular disc.

In some embodiments, the microcarrier is less than about 200 μm in diameter. For example, in some embodiments, the diameter of the microcarrier is less than about 200 μm, less than about 180 μm, less than about 160 μm, less than about 140 μm, less than about 120 μm, less than about 100 μm, less than about 80 μm, less than about 60 μm, less than about 40 μm, or less than about 20 μm.

In some embodiments, the diameter of the microcarrier is about 180 μm, about 160 μm, about 140 μm, about 120 μm, about 100 μm, about 90 μm, about 80 μm, about 70 μm, about 60 μm, about 50 μm, about 40 μm, about 30 μm, about 20 μm, or about 10 μm. In certain embodiments, the microcarrier is about 60 μm in diameter.

In some embodiments, the microcarrier is less than about 50 μm in thickness. For example, in some embodiments, the thickness of the microcarrier is less than about 70 μm, about 60 μm, about 50 μm, about 40 μm, about 30 μm, less than about 25 μm, less than about 20 μm, less than about 15 μm, less than about 10 μm, or less than about 5 μm. In some embodiments, the thickness of the microcarrier is less than about any of the following thicknesses (in μm): 70, 65, 60, 55, 50, 45, 40, 35, 30, 25, 20, 15, 10, 9, 8, 7, 6, 5, 4, 3, or 2. In some embodiments, the thickness of the microcarrier is greater than about any of the following thicknesses (in μm): 1, 2, 3, 4, 5, 6, 7, 8, 9, 10, 15, 20, 25, 30, 35, 40, 45, 50, 55, 60, or 65. That is, the thickness of the microcarrier may be any of a range of thicknesses (in μm) having an upper limit of 70, 65, 60, 55, 50, 45, 40, 35, 30, 25, 20, 15, 10, 9, 8, 7, 6, 5, 4, 3, or 2 and an independently selected lower limit of 1, 2, 3, 4, 5, 6, 7, 8, 9, 10, 15, 20, 25, 30, 35, 40, 45, 50, 55, 60, or 65, wherein the lower limit is less than the upper limit.

In some embodiments, the thickness of the microcarrier is about 50 μm, about 45 μm, about 40 μm, about 35 μm, about 30 μm, about 25 μm, about 20 μm, about 19 μm, about 18 μm, about 17 μm, about 16 μm, about 15 μm, about 14 μm, about 13 μm, about 12 μm, about 11 μm, about 10 μm, about 9 μm, about 8 μm, about 7 μm, about 6 μm, about 5 μm, about 4 μm, about 3 μm, about 2 μm, or about 1 μm. In certain embodiments, the microcarrier is about 10 μm in thickness.

In some aspects, a microcarrier of the present disclosure can comprise a capture agent. In some embodiments, the capture agent for a particular microcarrier species may be a "unique capture agent," e.g., a capture agent is associated with a particular microcarrier species having a particular identifier (e.g., analog code). The capture agent can be any biomolecule or a chemical compound capable of binding one or more analytes (such as a biomolecule or chemical compound) present in the solution. Examples of biomolecule capture agents include, but are not limited to, a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. Examples of chemical compound capture agents include, but are not limited to, individual components of chemical libraries, small molecules, or environmental toxins (for example, pesticides or heavy metals).

In some embodiments, the capture agent is coupled to a surface of the microcarrier (in some embodiments, in at least a center portion of the microcarrier surface). In some embodiments, the capture agent can be chemically attached to the microcarrier. In other embodiments, the capture agent can be physically absorbed to the surface of the microcarrier. In some embodiments, the attachment linkage between the capture agent and the microcarrier surface can be a covalent bond. In other embodiments, the attachment linkage between the capture agent and the microcarrier surface can be a non-covalent bond including, but not limited to, a salt bridge or other ionic bond, one or more hydrogen bonds, hydrophobic interactions, Van der Waals force, London dispersion force, a mechanical bond, one or more halogen bonds, aurophilicity, intercalation, or stacking.

In some aspects, more than one (such as two, three, four, five, six, seven, eight, nine, or ten) capture agents for the same analyte can each be associated with a microcarrier described herein. In this embodiment, each capture agent for a particular analyte binds to the analyte with a different affinity as measured by the dissociation constant of analyte/capture agent binding. Accordingly, within a plurality of microcarriers in a composition, there can be two or more subpopulations of microcarriers with capture agents that bind to the same analyte, but wherein the capture agents associated with each subpopulation bind to the analyte with a different affinity. In some embodiments, the dissociation constant of the analyte for any of the capture agents is not greater than $10^{-6}$M, such as $10^{-7}$M or $10^{-8}$M. In other embodiments, the dissociation constant of the analyte for any of the capture agents is from about $10^{-10}$ M to about $10^{-6}$M, such from about $10^{-10}$ M to about $10^{-7}$M, about $10^{-10}$ M to about $10^{-8}$M, about $10^{-10}$ M to about $10^{-9}$M, about $10^{-9}$ M to about $10^{-6}$M, about $10^{-9}$ M to about $10^{-7}$M, about $10^{-9}$ M to about $10^{-8}$M, about $10^{-8}$ M to about $10^{-6}$M, or about $10^{-8}$ M to about $10^{-7}$M. In some embodiments, the dissociation constant of the analyte for any two capture agents differs by as much as about 3 $\log_{10}$, such as by as much as about 2.5 $\log_{10}$, 2 $\log_{10}$, 1.5 $\log_{10}$, or 1 $\log_{10}$.

In some embodiments, an analyte of the present disclosure is coupled to a microcarrier for the capture of one or more analytes. In some embodiments, the one or more analytes may be captured from a sample, such as a biological sample described herein. In some embodiments, an analyte may include without limitation a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In other embodiments, the analyte is a chemical compound (such as a small molecule chemical compound) capable of binding to the capture agent such as individual components of chemical libraries, small molecules, or environmental toxins (for example, pesticides or heavy metals).

In some aspects, the analytes in a sample (such as a biological sample) can be labeled with a signal-emitting entity capable of emitting a detectable signal upon binding to the capture agent. In some embodiments, the signal-emitting entity can be colorimetric based. In other embodiments, the signal-emitting entity can be fluorescence-based including, but not limited to, phycoerythrin, blue fluorescent protein, green fluorescent protein, yellow fluorescent protein, cyan fluorescent protein, and derivatives thereof. In other embodiments, the signal-emitting entity can be radio-isotope based, including, but not limited to, molecules labeled with $^{32}P$, $^{33}P$, $^{22}Na$, $^{36}Cl$, $^{2}H$, $^{3}H$, $^{35}S$, and $^{123}I$. In other embodiments, the signal-emitting entity is light-based including, but not limited to, luciferase (e.g., chemiluminescence-based), horseradish peroxidase, alkaline phosphatase, and derivatives thereof. In some embodiments, the biomolecules or chemical compounds present in the sample can be labeled with the signal-emitting entity prior to contact with the microcarrier. In other embodiments, the biomolecules or chemical compounds present in the sample can be labeled with the signal-emitting entity subsequent to contact with the microcarrier.

IV. Methods of Making Encoded Microcarriers

Certain aspects of the present disclosure relate to methods for making an encoded microcarrier, e.g., a microcarrier described herein. The methods for making an encoded microcarrier may include one or more of the microcarrier features or aspects described herein, e.g., in section III above and/or the Examples that follow.

In some embodiments, the methods include depositing a substantially transparent polymer layer, where the substantially transparent polymer layer has a first surface and a second surface, the first and the second surfaces being parallel to each other In some embodiments, the first and the second surfaces that are parallel to each other may be the top and bottom surface of a single layer. Any suitable substantially transparent polymer known in the art or described herein may be used. In some embodiments, the substantially transparent polymer layer is deposited using spin coating.

In some embodiments, the substantially transparent polymer layer may be deposited on a substrate. Suitable substrates may include substrates used in standard semiconductor and/or micro-electro-mechanical systems (MEMS) fabrication techniques. In some embodiments, the substrate may comprise glass, silicon, quartz, plastic, polyethylene terephthalate (PET), an indium tin oxide (ITO) coating, or the like.

In some embodiments, a sacrificial layer may be deposited on the substrate, e.g., a substrate as described above. In some embodiments, the sacrificial layer may be made of a polymer, including without limitation polyvinyl alcohol (PVA) or OmniCoat™ (MicroChem; Newton, Mass.). Sacrificial layers may be applied, used, and dissolved or stripped, e.g., according to manufacturer's instructions.

In some embodiments, a substantially transparent polymer layer of the present disclosure is deposited on a sacrificial layer. To generate a planar microcarrier surface using a substantially transparent polymer layer, the substantially transparent polymer layer may be deposited onto a planar sacrificial layer. To generate a microcarrier surface with one or more colums projecting therefrom, a sacrificial layer (e.g., one deposited onto a substrate) may be patterned with one or more column-shaped holes or void areas, for example by using a standard lithographic process. In some embodiments, a substantially transparent polymer layer may be deposited over the sacrificial layer and optional substrate such that the layer is deposited in the one or more column-shaped holes or void areas. In some embodiments, another substantially transparent polymer layer may then be deposited over the sacrificial layer and the one or more column-shaped holes or void areas filled with the first substantially transparent polymer layer.

In some embodiments, a magnetic, substantially non-transparent layer of the present disclosure is deposited on the first surface of the substantially transparent polymer layer. In some embodiments, the magnetic, substantially non-transparent layer is deposited by sputtering. The magnetic, substantially non-transparent layer may be made of, e.g., any of the magnetic materials described herein. For example, in some embodiments, the magnetic, substantially non-transparent layer comprises nickel (e.g., elemental nickel, or an alloy thereof).

In some embodiments, the magnetic, substantially non-transparent layer may be etched to remove a portion of the magnetic, substantially non-transparent layer that is deposited over a center portion of the substantially transparent polymer layer. The magnetic, substantially non-transparent layer may be etched by any means known in the art. For example, in some embodiments, the magnetic, substantially non-transparent layer is etched by conventional wet etching. Exemplary dimensions, shapes, and optional asymmetries for a magnetic, substantially non-transparent layer are provided supra.

In some embodiments, a second substantially transparent polymer layer of the present disclosure is deposited over the magnetic, substantially non-transparent layer. In some embodiments, the second substantially transparent polymer layer has a first surface and a second surface that are parallel to each other (e.g., the top and bottom surface of a single layer). In some embodiments, the second surface is affixed to the magnetic, substantially non-transparent layer. In some embodiments, the second substantially transparent polymer layer is aligned with the first substantially transparent polymer layer and has a center portion that is aligned with the center portion of the substantially transparent polymer layer. Exemplary dimensions for the center portion of a substantially transparent polymer layer are provided supra.

In some embodiments, a substantially non-transparent polymer layer of the present disclosure is deposited on the first surface of the second substantially transparent polymer layer. In some embodiments, the substantially non-transparent polymer layer encloses the center portions of the first and the second substantially transparent polymer layers. In some embodiments, the substantially non-transparent polymer layer comprises a two-dimensional shape representing an analog code. Any of the two-dimensional shapes described or exemplified herein may be used, e.g., a gear shape of the present disclosure. In some embodiments, the substantially non-transparent polymer layer is deposited over the second substantially transparent polymer layer and etched (e.g., using a standard lithographic process) into the desired two-dimensional shape.

In some embodiments, one or more columns may be deposited on the substantially transparent polymer, e.g., on the first surface of the second substantially transparent polymer layer at a portion not covered by the substantially non-transparent polymer layer. The one or more columns may be deposited as described herein, e.g., using a standard lithographic process.

In some embodiments that employ an optional sacrificial layer and/or substrate of the present disclosure, the sacrificial layer may be dissolved or stripped, and/or the substrate may be removed, using a solvent. A variety of solvents useful for fabrication (e.g., in standard semiconductor or MEMS fabrication processes, such as photoresist removal) are known in the art. In some embodiments, the solvent is a photoresist stripper solvent, such as a DMSO- or 1-methyl-2-pyrrolidon (NMP)-based solvent. In some embodiments, the solvent is an AZ® photoresist stripper, such as AZ® 300T (AZ Electronic Materials; Somerville, N.J.).

In some embodiments, the methods include depositing a sacrificial layer of the present disclosure on a substrate of the present disclosure. Sacrificial layers, substrates, and suitable deposition methods are described, e.g., as above.

In some embodiments, a substantially non-transparent polymer layer of the present disclosure is deposited on the sacrificial layer. In some embodiments, the substantially non-transparent polymer layer has a first and a second surface that are parallel to each other (e.g., the top and bottom surface of a single layer). In some embodiments, the second surface is affixed to the sacrificial layer.

In some embodiments, the outline of the substantially non-transparent polymer layer is shaped into a two-dimensional shape representing an analog code, e.g., as described herein. The substantially non-transparent polymer layer may be shaped by any method known in the art or described herein, e.g., using a standard lithographic process including but not limited to spin coating, soft baking, UV exposure, etching, and hard baking.

In some embodiments, the sacrificial layer may be dissolved or stripped, and/or the substrate may be removed, using a solvent, e.g., as described above.

In other embodiments, a magnetic layer comprising a magnetic material of the present disclosure is deposited on the sacrificial layer. Exemplary magnetic materials, magnetic layer shapes/dimensions, and deposition methods related thereto are provided supra. For example, in some embodiments, the magnetic layer may be shaped into one or more columns, e.g., as illustrated by column 906. In other embodiments, the magnetic layer may be between two non-transparent polymer layers, e.g., embedded as illustrated by magnetic layer 704. The magnetic material may contain, e.g., any of the magnetic materials described herein. For example, in some embodiments, the magnetic material comprises nickel (e.g., elemental nickel, or an alloy thereof).

In some embodiments, a substantially non-transparent polymer layer of the present disclosure is deposited on the magnetic layer. In some embodiments, the substantially non-transparent polymer layer has a first and a second surface that are parallel to each other (e.g., the top and bottom surface of a single layer). In some embodiments, a surface (e.g., the second surface) of the substantially non-transparent polymer layer is affixed to the magnetic layer.

In some embodiments, the outline of the substantially non-transparent polymer layer is shaped into a two-dimensional shape representing an analog code, e.g., as described above.

In some embodiments, the sacrificial layer may be dissolved or stripped, and/or the substrate may be removed, using a solvent, e.g., as described above.

Exemplary microcarrier shapes, dimensions, and optional features suitable for the methods described above are provided throughout the present disclosure.

In some embodiments, a capture agent may be coupled to a microcarrier of the present disclosure, e.g., a microcarrier described herein and/or a microcarrier produced by any of the methods described herein. Any of the capture agents described herein, or any capture agent known in the art suitable for capturing an analyte described herein, may find use in the methods and/or microcarriers of the present disclosure.

In some embodiments, the capture agent may be coupled to a polymer layer of the present disclosure, e.g., a substantially transparent or substantially non-transparent polymer layer described herein. In some embodiments, the capture agent may be coupled to one or both of a first or a second surface of the polymer layer. In some embodiments, the capture agent may be coupled to at least the center portion of the polymer layer (e.g., a center portion as described herein). In some embodiments, the polymer comprises an epoxy-based polymer or otherwise contains an epoxide group.

In some embodiments, coupling the capture agent involves reacting the polymer with a photoacid generator and light to generate a cross-linked polymer. In some embodiments, the light is of a wavelength that activates the photoacid generator, e.g., UV or near-UV light. Photoacid generators are commercially available from Sigma-Aldrich (St. Louis) and BASF (Ludwigshafen). Any suitable photoacid generator known in the art may be used, including without limitation triphenyl or triaryl sulfonium hexafluoroantimonate; triarylsulfonium hexafluorophosphate; triphenylsulfonium perfluoro-1-butanesulfonate; triphenylsulfonium triflate; Tris(4-tert-butylphenyl)sulfonium perfluoro-1-butanesulfonate or triflate; Bis(4-tert-butylphenyl)iodonium-containing photoacid generators such as Bis(4-tert-butylphenyl)iodonium perfluoro-1-butanesulfonate, p-toluenesulfonate, and triflate; Boc-methoxyphenyldiphenylsulfonium triflate; (tert-Butoxycarbonylmethoxynaphthyl)-diphenylsulfonium triflate; (4-tert-Butylphenyl)diphenylsulfonium triflate; diphenyliodonium hexafluorophosphate, nitrate, perfluoro-1-butanesulfonate, triflate, or p-toluenesulfonate; (4-fluorophenyl)diphenylsulfonium triflate; N-hydroxynaphthalimide triflate; N-hydroxy-5-norbornene-2,3-dicarboximide perfluoro-1-butanesulfonate; (4-iodophenyl)diphenylsulfonium triflate; (4-methoxyphenyl)diphenylsulfonium triflate; 2-(4-methoxystyryl)-4,6-bis(trichloromethyl)-1,3,5-triazine; (4-methylphenyl)diphenylsulfonium triflate; (4-methylthiophenyl) methyl phenyl sulfonium triflate; (4-phenoxyphenyl) diphenylsulfonium triflate; (4-phenylthiophenyl) diphenylsulfonium triflate; or any of the photoacid generators described in product-finder.basf.com/group/corporate/product-finder/de/literature-documentIBrand+Irgacure-Brochure--Photoacid+Generator+Selection+Guide-English.pdf. In some embodiments, the photoacid generator is a sulfonium-containing photoacid generator.

In some embodiments, coupling the capture agent involves reacting an epoxide of the cross-linked polymer with a functional group such as an amine, carboxyl, thiol, or the like. Alternatively, the epoxy group on the surface can be oxidized to hydroxyl group, which is subsequently used as initiation sites for graft polymerization of water soluble polymers such as poly(acrylic acid). The carboxyl groups in poly(acrylic acid) are then used to form covalent bonds with amino or hydroxyl groups in capture agents.

In some embodiments, coupling the capture agent involves reacting an epoxide of the cross-linked polymer with a compound that contains an amine and a carboxyl. In some embodiments, the amine of the compound reacts with the epoxide to form a compound-coupled, cross-linked polymer. Without wishing to be bound to theory, it is thought that the capture agent may be coupled to the polymer before the polymer is cross-linked; however, this may reduce the uniformity of the resulting surface. Any compound with a primary amine and a carboxyl group may be used. Compounds may include without limitation glycine, amino undecanoic acid, amino caproic acid, acrylic acid, 2-carboxyethyl acrylic acid, vinylbenzoic acid, 3-acrylamide-3-methyl-1-butanoic acid, glycidyl methacrylate, and the like. In some embodiments, the carboxyl of the compound-coupled, cross-linked polymer reacts with an amine (e.g., a primary amine) of the capture agent to couple the capture agent to the substantially transparent polymer.

Descriptions of various capture agents and analytes suitable for the methods described above may be found throughout the present disclosure, e.g., in section III above and/or the Examples that follow.

V. Multiplex Assays

Certain aspects of the present disclosure relate to methods for detecting analytes in a solution by using an encoded microcarrier, e.g., a microcarrier described herein. The methods for analyte detection using an encoded microcarrier that includes one or more of the microcarrier features or aspects described herein, e.g., in sections III and IV above and/or the Examples that follow. Advantageously, these encoded microcarriers allow for analyte detection in improved multiplex assays with a large number of potential unique microcarriers and reduced recognition error, as compared to traditional multiplex assays. The analyte detection methods used herein may be performed in any suitable assay vessel known in the art, for example a microplate, petri dish, or any number of other well-known assay vessels.

In some embodiments, the methods for detecting analytes in a solution comprise contacting a solution comprising a first analyte and a second analyte with a plurality of microcarriers, where the plurality of microcarriers comprises at least a first microcarrier of the present disclosure that specifically captures the first analyte and is encoded with a first analog code, and a second microcarrier of the present disclosure that specifically captures the second analyte and is encoded with a second analog code; decoding the first analog code and the second analog code using analog shape recognition to identify the first microcarrier and the second microcarrier; and detecting an amount of the first analyte bound to the first microcarrier and an amount of the second analyte bound to the second microcarrier.

In some embodiments, the methods include contacting a solution comprising a first analyte and a second analyte with a plurality of microcarriers. In some embodiments, the plurality of microcarriers may include a first microcarrier of the present disclosure that specifically captures the first analyte (e.g., using a capture agent, coupled to the microcarrier, specific for the first analyte), where the first microcarrier is encoded with a first analog code; and a second microcarrier of the present disclosure that specifically captures the second analyte (e.g., using a capture agent, coupled to the microcarrier, specific for the second analyte), where the second microcarrier is encoded with a second analog code different from the first analog code. In some embodiments, the first and second analytes may be different. In other embodiments, the first and second analytes may be the same, e.g., the first and second microcarriers may redundantly recognize the same analyte (this may be useful, e.g., for quality control purposes), or they may recognize distinct regions of the same analyte (e.g., antibodies recognizing different epitopes of the same antigen).

The methods of the present disclosure may be used to detect analytes in any suitable solution. In some embodiments, the solution comprises a biological sample. Examples of biological samples include without limitation blood, urine, sputum, bile, cerebrospinal fluid, interstitial fluid of skin or adipose tissue, saliva, tears, bronchial-alveolar lavage, oropharyngeal secretions, intestinal fluids, cervicovaginal or uterine secretions, and seminal fluid. In some embodiments, the biological sample may be from a human. In other embodiments, the solution comprises a sample that is not a biological sample, such as an environmental sample, a sample prepared in a laboratory (e.g., a sample containing one or more analytes that have been prepared, isolated, purified, and/or synthesized), a fixed sample (e.g., a formalin-fixed, paraffin-embedded or FFPE sample), and so forth.

In some embodiments, the analysis is multiplexed, that is, each solution (e.g., a sample) is analyzed so that a signal from the signal emitting entity is detected by the reaction detection system for at least 2 analytes of interest, at least 3 analytes of interest, at least 4 analytes of interest, at least 5 analytes of interest, at least 10 analytes of interest, at least 15 analytes of interest, at least 20 analytes of interest, at least 25 analytes of interest, at least 30 analytes of interest, at least 35 analytes of interest, at least 40 analytes of interest, at least 45 analytes of interest, or at least 50 analytes of interest, or more.

In some embodiments, the methods include decoding the first analog code and the second analog code using analog shape recognition to identify the first microcarrier and the second microcarrier. Conceptually, this decoding may involve imaging the analog code of each microcarrier (e.g., in a solution or sample), comparing each image against a library of analog codes, and matching each image to an image from the library, thus positively identifying the code. Optionally, as described herein, when using microcarriers that include an orientation indicator (e.g., an asymmetry), the decoding may further include a step of rotating each image to align with a particular orientation (based in part, e.g., on the orientation indicator). For example, if the orientation indicator includes a gap, the image could be rotated until the gap reaches a predetermined position or orientation (e.g., a 0° position of the image).

Various shape recognition software, tools, and methods are known in the art. Examples of such APIs and tools include without limitation Microsoft® Research FaceSDK, OpenBR, Face and Scene Recognition from ReKognition, Betaface API, and various ImageJ plugins. In some embodiments, the analog shape recognition may include without limitation image processing steps such as foreground extraction, shape detection, thresholding (e.g., automated or manual image thresholding), and the like.

It will be appreciated by one of skill in the art that the methods and microcarriers described herein may be adapted for various imaging devices, including without limitation a microscope, plate reader, and the like. In some embodiments, decoding the analog codes may include illuminating the first and second microcarriers by passing light through the substantially transparent portions (e.g., substantially transparent polymer layer(s)) of the first and second microcarriers and/or the surrounding solution. The light may then fail to pass through, or pass through with a lower intensity or other appreciable difference, the substantially non-transparent portions (e.g., substantially non-transparent polymer layer(s)) of the first and second microcarriers to generate a first analog-coded light pattern corresponding to the first microcarrier and a second analog-coded light pattern corresponding to the second microcarrier.

As described supra, any type of light microscopy may be used for the methods of the present disclosure, including without limitation one or more of: bright field, dark field, phase contrast, differential interference contrast (DIC), Nomarski interference contrast (NIC), Nomarski, Hoffman modulation contrast (HMC), or fluorescence microscopy. In certain embodiments, the analog codes may be decoded using bright field microscopy, and analyte(s) may be detected using fluorescence microscopy.

In some embodiments, decoding the analog codes may further include imaging the first analog-coded light pattern to generate a first analog-coded image and imaging the second analog-coded light pattern to generate a second analog-coded image. That is to say, the pattern of imaged light may correspond to the pattern of substantially transparent/substantially non-transparent areas of the microcarrier, thus producing an image of the analog codes. This imaging may include steps including without limitation capturing the image, thresholding the image, and any other image processing step desired to achieve more accurate, precise, or robust imaging of the analog codes.

In some embodiments, decoding the analog codes may further include using analog shape recognition to match the first analog-coded image with the first analog code and to match the second analog-coded image with the second analog code. In some embodiments, an image may be matched with an analog code (e.g., an image file from a library of image files, with each image file corresponding to a unique two-dimensional shape/analog code) within a predetermined threshold, e.g., that tolerates a predetermined amount of deviation or mismatch between the image and the exemplar analog code image. Such a threshold may be empirically determined and may naturally be based on the particular type of two-dimensional shapes used for the analog codes and the extent of variation among the set of potential two-dimensional shapes.

In some embodiments, the methods include detecting an amount of the first analyte bound to the first microcarrier and an amount of the second analyte bound to the second microcarrier. Any suitable analyte detection technique(s) known in the art may be used. For example, in some embodiments, the first and the second microcarriers may be incubated with one or more detection agents. In some embodiments, the one or more detection agents bind the first analyte captured by the first microcarrier and the second analyte captured by the second microcarrier. In some embodiments, the methods further include measuring the amount of detection agent bound to the first and the second microcarriers.

In some embodiments, the analytes in a solution (such as a biological sample) can be labeled with a detection agent (e.g., a signal-emitting entity) capable of emitting a detectable signal upon binding to the capture agent. In some embodiments, the detection agent can be colorimetric based. In other embodiments, the detection agent can be fluorescence-based including, but not limited to, phycoerythrin, blue fluorescent protein, green fluorescent protein, yellow fluorescent protein, cyan fluorescent protein, and derivatives thereof. In other embodiments, the detection agent can be radioisotope based, including, but not limited to, molecules labeled with $^{32}P$, $^{33}P$, $^{22}Na$, $^{36}Cl$, $^{2}H$, $^{3}H$, $^{35}S$, and $^{123}I$. In other embodiments, the detection agent is light-based including, but not limited to, luciferase (e.g. chemiluminescence-based), horseradish peroxidase, alkaline phosphatase and derivatives thereof. In some embodiments, the biomolecules or chemical compounds present in the solution can be labeled with the detection agent prior to contact with the microcarrier composition. In other embodiments, the biomolecules or chemical compounds present in the solution can be labeled with the detection agent subsequent to contact with the microcarrier composition. In yet other embodiments, the detection agent may be coupled to a molecule or macromolecular structure that specifically binds the analyte of interest, e.g., a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and/or an antibody fragment.

In some embodiments, the detection agent is a fluorescent detection agent, and the amount of detection agent bound to the first and the second microcarriers is measured by fluorescence microscopy (e.g., a fluorescent microscope or plate reader). In other embodiments, the detection agent is a luminescent detection agent, and the amount of detection agent bound to the first and the second microcarriers is measured by luminescence microscopy (e.g., a luminescent microscope or plate reader).

In some embodiments, each analyte/capture agent may be used with a specific detection agent. As non-limiting examples, the detection agent may be a detection agent (e.g., a fluorescent, luminescent, enzymatic, or other detection agent) coupled to an antibody that specifically binds the analyte; or a ligand or receptor of a ligand-receptor pair, if the analyte is a cognate ligand/receptor of the ligand-receptor pair. This technique is conceptually similar to a sandwich ELISA or protein microarray that includes a capture and a detection antibody (though it should be noted in the present case that the agents in this example are not strictly limited to antibodies). As another non-limiting example, the detection agent may be a fluorescent or other detectable probe coupled to a protein of interest, such as a labeled analyte of interest. For example, a reaction may be used to couple detection agent(s) to one or more proteins in a solution of interest (e.g., a sample), which would then be captured by the capture agents (conceptually similar to an antigen capture-type of protein microarray).

In other embodiments, multiple unique analytes/capture agents may be used with a universal detection agent. As non-limiting examples, the detection agent may be an agent that binds to the Fc region of an antibody, if the analyte is an antibody; a fluorescent or other detectable probe coupled to an oligonucleotide (e.g., a single stranded oligonucleotide that hybridizes with an analyte), if the analyte is a polynucleotide such as DNA or RNA. The later scenario is conceptually similar to a microarray technique.

In some embodiments, the detecting steps may include one or more washing steps, e.g., to reduce contaminants, remove any substances non-specifically bound to the capture agent and/or microcarrier surface, and so forth. In some embodiments, a magnetic separation step may be used to wash a microcarrier containing a magnetic layer or material of the present disclosure. In other embodiments, other separation steps known in the art may be used.

In some embodiments, the decoding step(s) may occur after the detecting step(s). In other embodiments, the decoding step(s) may occur before the detecting step(s). In still other embodiments, the decoding step(s) may occur simultaneously with the detecting step(s).

VI. Kits or Articles of Manufacture

Further provided herein are kits or articles of manufacture containing a plurality of microcarriers of the present disclosure. These kits or articles of manufacture may find use, inter alia, in conducting a multiplex assay, such as the exemplary multiplex assays described herein (see, e.g., section V above).

In some embodiments, the kits or articles of manufacture may include a first microcarrier of the present disclosure that specifically captures a first analyte (e.g., using a capture agent, coupled to the microcarrier, specific for the first analyte), where the first microcarrier is encoded with a first analog code; and a second microcarrier of the present disclosure that specifically captures the second analyte (e.g., using a capture agent, coupled to the microcarrier, specific for the second analyte), where the second microcarrier is encoded with a second analog code different from the first analog code. In some embodiments, the first and second analytes may be different. In other embodiments, the first and second analytes may be the same, e.g., the first and second microcarriers may redundantly recognize the same analyte (this may be useful, e.g., for quality control purposes), or they may recognize distinct regions of the same analyte (e.g., antibodies recognizing different epitopes of the same antigen). The kits or articles of manufacture may include any of the microcarriers described herein (see, e.g., section III above and the Examples infra) or produced using the methods described herein (see, e.g., section IV above and the Examples infra).

In some embodiments, the kits or articles of manufacture may further include one or more detection agents of the present disclosure for detecting an amount of the first analyte bound to the first microcarrier and an amount of the second analyte bound to the second microcarrier. In some embodiments, the detection agent for the first analyte may be the same as the detection agent for the second analyte. In other embodiments, the detection agent for the first analyte may be different from the detection agent for the second analyte.

In some embodiments, the kits or articles of manufacture may further include instructions for using the kit or articles of manufacture to detect one or more analytes, e.g., the first and the second analyte. These instructions may be for using the kit or article of manufacture, e.g., in any of the methods described herein.

In some embodiments, the kits or articles of manufacture may further include one or more detection agents (e.g., as described above), along with any instructions or reagents suitable for coupling a detection agent to one or more analytes, or for coupling a detection agent to one or more macromolecules that recognize an analyte. The kits or articles of manufacture may further include any additional components for using the microcarriers in an assay (e.g., a multiplex assay), including without limitation a plate (e.g., a 96-well or other similar microplate), dish, microscope slide, or other suitable assay container; a non-transitory computer-readable storage medium (e.g., containing software and/or other instructions for analog shape or code recognition); washing agents; buffers; plate sealers; mixing containers; diluents or storage solutions; and the like.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Attention is now directed towards microcarriers for multiplex assays (e.g., analyte detection) and their methods of production. The following Examples illustrate exemplary embodiments of analog-encoded microcarriers for analyte detection that may find use, inter alia, in the methods, assays, and kits or articles of manufacture described herein. It is to be noted that these exemplary embodiments are in no way intended to be limiting but are provided to illustrate some of the aspects and features set forth herein.

Example 1: Encoded Microcarriers with a Two-Dimensional, Analog Code and Uniform Shape As described above, analog-encoded microcarriers are highly advantageous for multiplexed assays due to the vast number of potential unique identifiers and reduced recognition error. This Example describes various types of microcarriers encoded with a two-dimensional shape, which may be used as an analog code for identification. It is to be understood that the encoded microcarriers of the present disclosure may include some or all of the optional features set forth below in any combination.

Figure 1B:
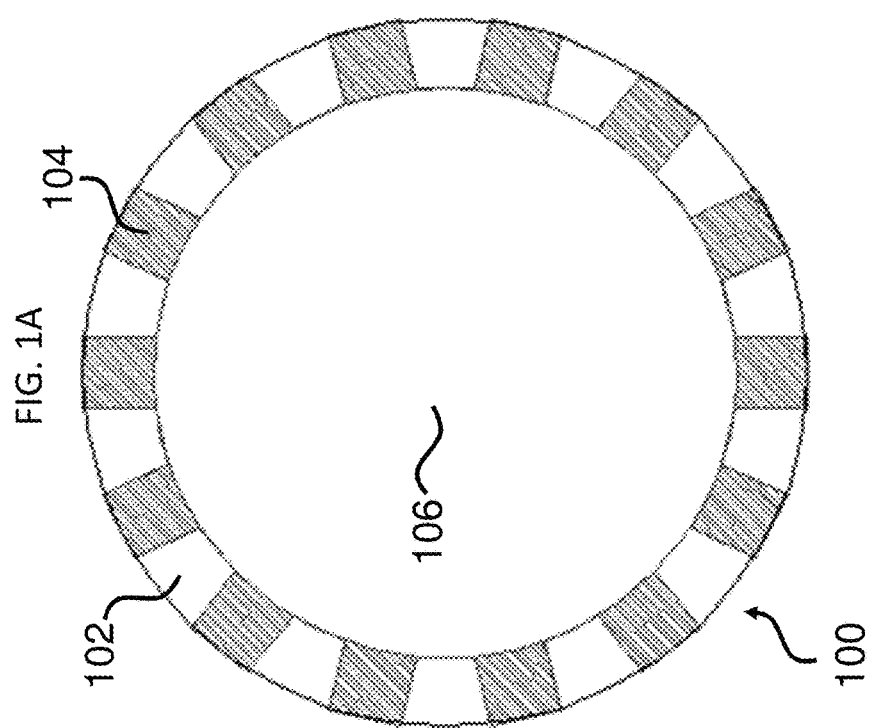

FIGS. 1A & 1B show two views of exemplary microcarrier 100. Microcarrier 100 is a circular disc of approximately 50 µm in diameter and 10 µm in thickness. FIG. 1A provides a view of microcarrier 100 looking at a circular face of the disc, while FIG. 1B shows a side view of microcarrier 100 orthogonal to the surface shown in FIG. 1A. Two components of microcarrier 100 are shown. First, substantially transparent polymer layer 102 provides the body of the microcarrier. Layer 102 may be produced, e.g., using a polymer such as SU-8, as described above.

Substantially non-transparent polymer layer 104 is affixed to a surface of layer 102. While the cross-section of microcarrier 100 shown in FIG. 1B shows a discontinuous view of layer 104, the view shown in FIG. 1A illustrates that layer 104 is shaped like a circular gear with a plurality of teeth. The shape, number, size, and spacing of these gear teeth constitutes a two-dimensional shape, and one or more of these aspects of the gear teeth may be modified in order to produce multiple two-dimensional shapes for analog encoding. Advantageously, the outside edge of layer 104's gear teeth fit within the perimeter of layer 102. This allows for a variety of analog codes, each representing a unique identifier for one species of microcarrier, while maintaining a uniform overall shape across multiple species of microcarrier. Stated another way, each microcarrier species within a population of multiple species may have a different two-dimensional gear shape (i.e., analog code), but each microcarrier will have the same perimeter, leading to greater uniformity of physical properties (e.g., size, shape, behavior in solution, and the like). Layer 104 may be produced, e.g., using a polymer such as SU-8 mixed with a dye, or using a black matrix resist, as described above.

Layer 104 surrounds center portion 106 of layer 102. A capture agent for capturing an analyte is coupled to at least center portion 106 on one or both surfaces (i.e., upper/lower surfaces) of layer 102. Advantageously, this allows center portion 106 to be imaged without any potential for interference resulting from layer 104.

FIGS. 1C & 1D show an exemplary assay using microcarrier 100 for analyte detection. FIG. 1C shows that microcarrier 100 may include capture agent 108 coupled to one or more surfaces in at least center portion 106. Microcarrier 100 is contacted with a solution containing analyte 110, which is captured by capture agent 108. As described above, various capture agents may be used to capture different types of analytes, ranging from small molecules, nucleic acids, and proteins (e.g., antibodies) to organelles, viruses, and cells. FIG. 1C illustrates a single microcarrier species (i.e., microcarrier 100), which captures analyte 110, but in a multiplex assay multiple microcarrier species are used, each species having a particular capture agent that recognizes a specific analyte.

FIG. 1D illustrates an exemplary process for "reading" microcarrier 100. This process includes two steps that may be accomplished simultaneously or separately. First, the capture of analyte 110 by capture agent 108 is detected. In the example shown in FIG. 1D, detection agent 114 binds to analyte 110. Analyte not captured by a capture agent coupled to microcarrier 100 may have been washed off prior to detection, such that only analytes bound to microcarrier 100 are detected. Detection agent 114 also includes a reagent for detection. As one example, detection agent 114 may include a fluorophore that, when excited by light 116 at a wavelength within the excitation spectrum of the fluorophore, emits light 118 (e.g., a photon). Light 118 may be detected by any suitable detection means, such as a fluorescence microscope, plate reader, and the like.

In addition, microcarrier 100 is read for its unique identifier. In the example shown in FIG. 1D, light 112 is used to illuminate the field containing microcarrier 100 (in some embodiments, light 112 may have a different wavelength than lights 116 and 118). When light 112 illuminates the field containing microcarrier 100, it passes through substantially transparent polymer layer 102 but is blocked by substantially non-transparent polymer layer 104, as shown in FIG. 1D. This generates a light pattern that can be imaged, for example, by light microscopy (e.g., using differential interference contrast, or DIC, microscopy). This light pattern is based on the two-dimensional shape (i.e., analog code) of microcarrier 100. Standard image recognition techniques may be used to decode the analog code represented by the image of microcarrier 100.

The analyte detection and identifier imaging steps may occur in any order, or simultaneously. Advantageously, both detection steps shown in FIG. 1D may be accomplished on one imaging device. As one example, a microscope capable of both fluorescence and light (e.g., bright field) microscopy may be used to quantify the amount of analyte 110 bound to microcarrier 100 (e.g., as detected by detection agent 114) and image the analog code created by layers 102 and 104. This allows for a more efficient assay process with fewer equipment requirements.

Turning now to FIGS. 2A & 2B, another exemplary microcarrier 200 is shown. Like microcarrier 100, microcarrier 200 includes substantially transparent polymer layer 202 and substantially non-transparent polymer layer 204. In addition, microcarrier 200 includes magnetic layer 206. As shown in FIG. 2A, magnetic layer 206 may be shaped as a ring between center portion 208 and substantially non-transparent layer 204.

FIG. 2B shows that magnetic layer 206 may be embedded within layer 202. Layer 202 may also include more than one layer, such that magnetic layer 206 is sandwiched between two substantially transparent polymer layers (e.g., as in FIG. 2B). Alternatively, magnetic layer 206 may be affixed to the same surface of layer 202 as layer 204, or magnetic layer 206 may be affixed to the surface of layer 202 opposite layer 204. In some embodiments, magnetic layer 206 may include nickel.

Magnetic layer 206 bestows magnetic properties onto microcarrier 200, which advantageously may be used for many applications. For example, microcarrier 200 may be affixed to a surface by magnetic attraction during a washing step, allowing for effective washing without losing or otherwise disrupting the microcarriers.

In addition to its magnetic properties, layer 206 is also substantially non-transparent. When imaged as shown in FIG. 1D (e.g., using light 112), layer 206 will block, either in part or in whole, transmitted light, thereby creating a pattern for imaging. As shown in FIG. 2A, layer 206 is also asymmetric—in this example, it includes gap 210. This asymmetry creates an orientation indicator that can be imaged, for example, as shown in FIG. 1D using light 112. Advantageously, an orientation indicator may be utilized during image recognition to orient the two-dimensional shape created by imaging layer 204 in a uniform orientation for easier analog code recognition. This allows microcarriers imaged in any orientation to be decoded.

Figure 3:
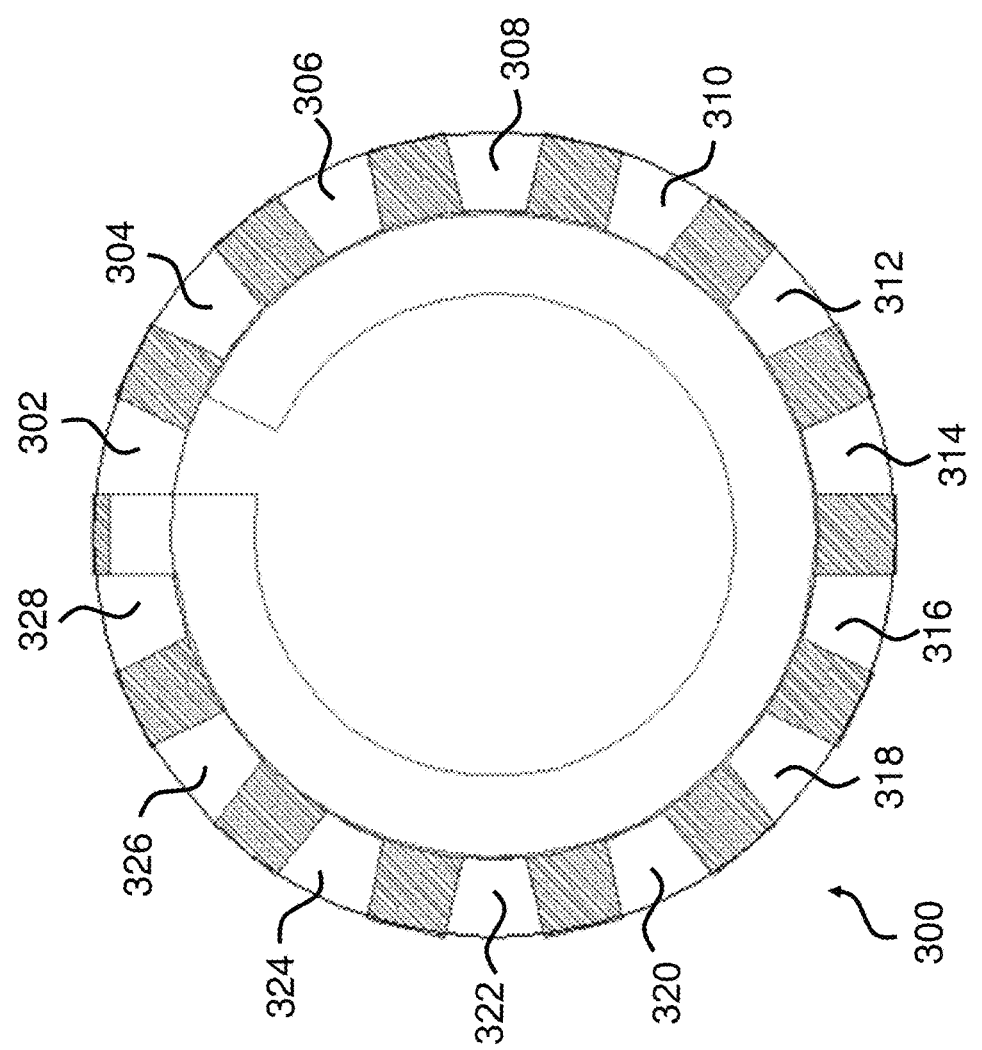
FIG. 3 shows an exemplary analog encoding scheme that includes multiple shape variation points for generating unique analog codes.

FIG. 3 shows the vast number of potential analog codes possible using the gear shape shown in FIGS. 1A-2B. FIG. 3 illustrates an exemplary coding scheme in which multiple shape variation points are labeled, e.g., at positions 302, 304, 306, 308, 310, 312, 314, 316, 318, 320, 322, 324, 326, and 328 on exemplary microcarrier 300. Even if a simple "filled or not filled" scheme is used, up to $2^{14}$ unique codes are possible based on the use of 14 shape variation points. This scheme is convenient for both manufacturing and for generating two-dimensional shapes that are easily distinguishable for image recognition analysis. However, since analog encoding is used, more complex schemes using more than 2 possibilities (e.g., at each shape variation point as labeled in FIG. 3) are possible, thereby exponentially expanding the number of unique identifiers. For example, multiple gear tooth shapes and/or multiple sizes of gear teeth are possible. A two-dimensional gear shape as shown in FIGS. 1A-3 facilitates a wide range of unique analog codes while providing a large center portion (e.g., center portions 106 and 208) for analyte detection.

Figure 4A:
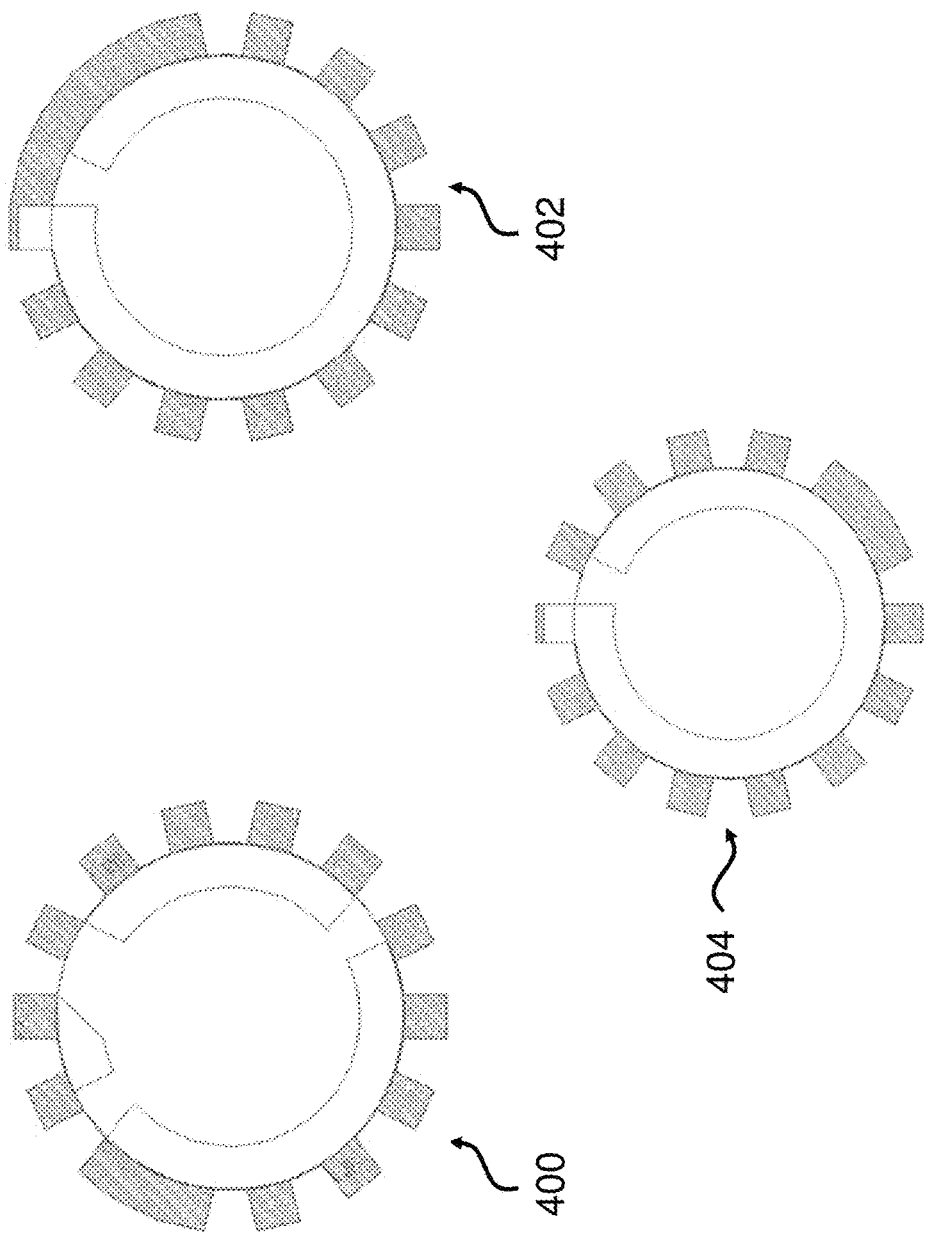
FIG. 4A shows three examples of microcarriers, each having a unique analog code.
Figure 4B:
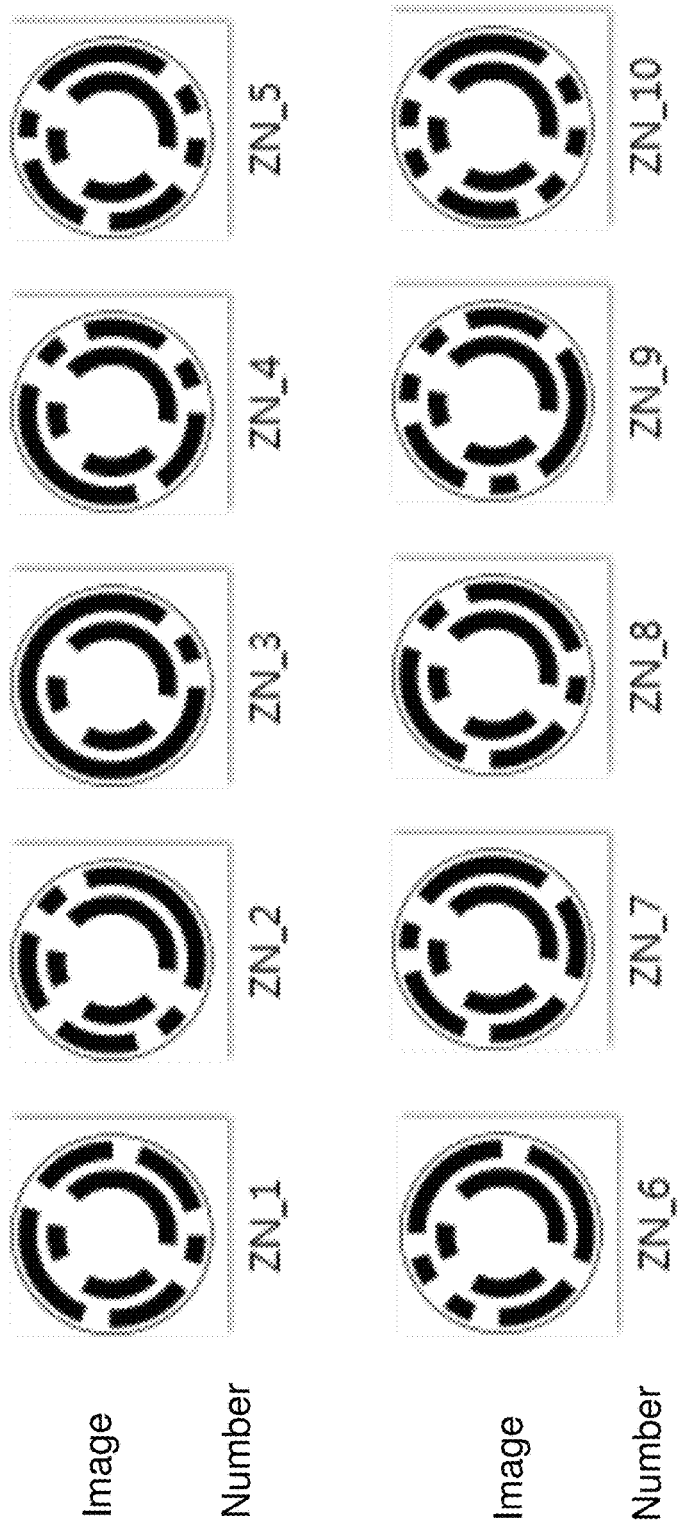
FIG. 4B shows examples of microcarriers with a unique analog code, in accordance with some embodiments.

FIG. 4A illustrates three exemplary embodiments of the coding scheme shown in FIG. 3: microcarriers 400, 402, and 404. The unique codes of microcarriers 400, 402, and 404 are generated using the simple "filled or not filled" scheme of FIG. 3. FIG. 4B illustrates 10 exemplary embodiments of the cod, inter alia, in terms of number of shapes (e.g., two distinct shapes in code ZN_3, as compared to seven distinct shapes in code ZN_10) and/or size of shapes (e.g., large, small, and intermediate-sized shapes in code ZN_2). Importantly, as described above, more complex encoding schemes are available using analog image recognition, thereby greatly expanding the number of potential unique codes.

Turning now to FIGS. 5A & 5B, another exemplary microcarrier 500 is shown. Like microcarrier 200, microcarrier 500 includes substantially transparent polymer layer 502, substantially non-transparent polymer layer 504, magnetic layer 506, and center portion 508. In addition, microcarrier 500 has four columns including column 510, which may be of any shape that extends from the surface of layer 502. As shown in FIG. 5A, these columns may be arrayed in alignment with magnetic layer 506, preventing any potential for interfering with analyte detection in center portion 508 or with reading the two-dimensional shape (i.e., the analog code) of layer 504. FIG. 5B shows that these columns may extend from the upper and lower surfaces of microcarrier 500. Column 510 may be made, for example, using the same substantially transparent polymer as layer 502 (exemplary methods of production are described infra). Advantageously, one or more columns such as column 510 may be used to prevent microcarriers from sticking to each other and/or a container (e.g., the side of a well in a multiwell plate), e.g., through optical contact bonding.

Example 2: Microcarriers with a Two-Dimensional, Analog Code Encoded in the Microcarrier Shape The previous Example illustrates multiple exemplary embodiments of microcarriers in which an analog code is provided by a non-transparent layer affixed to a transparent polymer layer. This is advantageous, for example, in allowing greater uniformity between different species of microcarriers (i.e., each has the same perimeter shape provided by the transparent polymer layer).

However, it may be advantageous for other reasons to use the perimeter of the microcarrier itself as the two-dimensional shape for analog encoding. For example, if the analog code is provided by the shape of the microcarrier itself, only one layer is required, thereby streamlining the manufacturing process. Moreover, shaping the perimeter of the microcarrier may be accomplished by highly precise manufacturing techniques, allowing a highly reproducible shape for more accurate image recognition.

FIGS. 6A & 6B show exemplary microcarrier 600 of this type. Microcarrier 600 is a gear-shaped disc approximately 80 μm in diameter and 15 μm in height, including optional column elements (similar to column 510 as described above). Microcarrier 600 is made of a single, non-transparent polymer layer 602, rather than separate transparent and non-transparent polymer layers. Microcarrier 600 may be imaged as shown in FIG. 1D, but its analog code is imaged based on the entire microcarrier shape (e.g., perimeter of the non-transparent polymer layer). One or both surfaces of microcarrier 600 may be used for coupling a capture agent as above, and a center portion or the entire surface may be used.

Figure 6C:
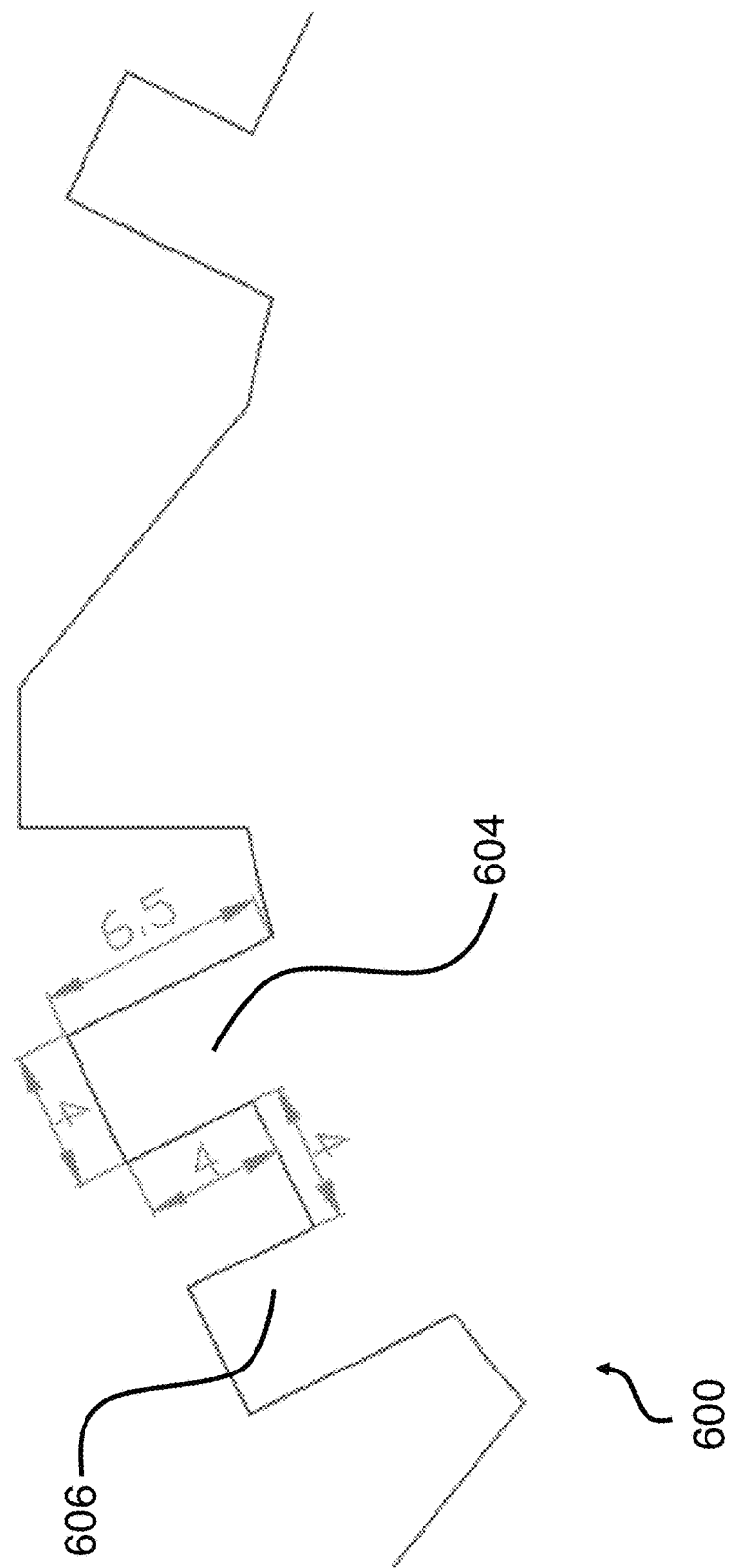
FIG. 6C shows the dimensions of an exemplary analog code. Dimensions are based on μm units.

FIG. 6C illustrates the dimensions of gear tooth 604 of microcarrier 600. As shown, in this embodiment, gear tooth 604 is 4 μm wide and spaced 4 μm from adjacent gear tooth 606. Since the two-dimensional shape of microcarrier 600 is analog encoded, the perimeter between adjacent gear teeth may be variable, allowing for multiple gear tooth shapes. For example, gear tooth 604 extends 4 or 6.5 μm in height, relative to the adjacent perimeter segment immediately to the left or right, respectively.

Figure 7:
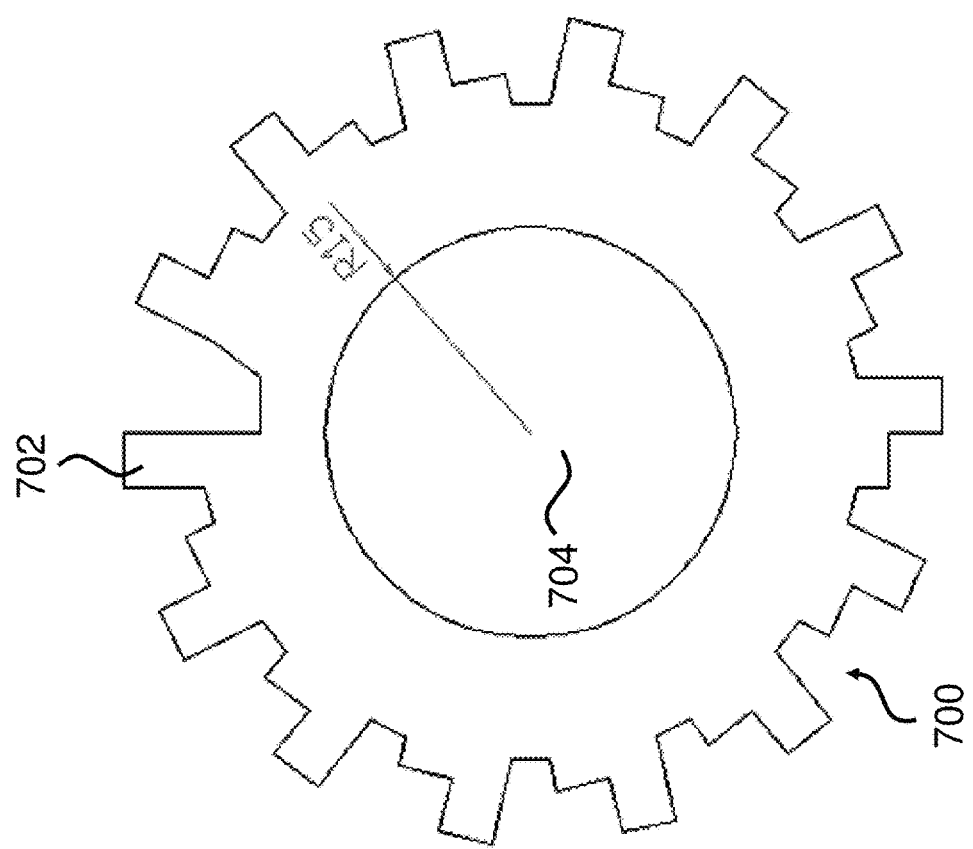
FIG. 7 shows an exemplary microcarrier.

FIG. 7 illustrates another embodiment of this type of microcarrier, microcarrier 700. Like microcarrier 600, microcarrier 700 is made from non-transparent polymer layer 702. In addition, microcarrier includes magnetic layer 704. Magnetic layer 704 may be affixed to one of the surfaces of microcarrier 700, or it may be embedded within microcarrier 700 (e.g., between two non-transparent polymer layers). Magnetic layer 704 may be generated, for example, by depositing nickel. As described above, a magnetic layer allows additional functionalities, such as the option for washing microcarrier 700 while magnetically attached to another surface.

Figure 8A:
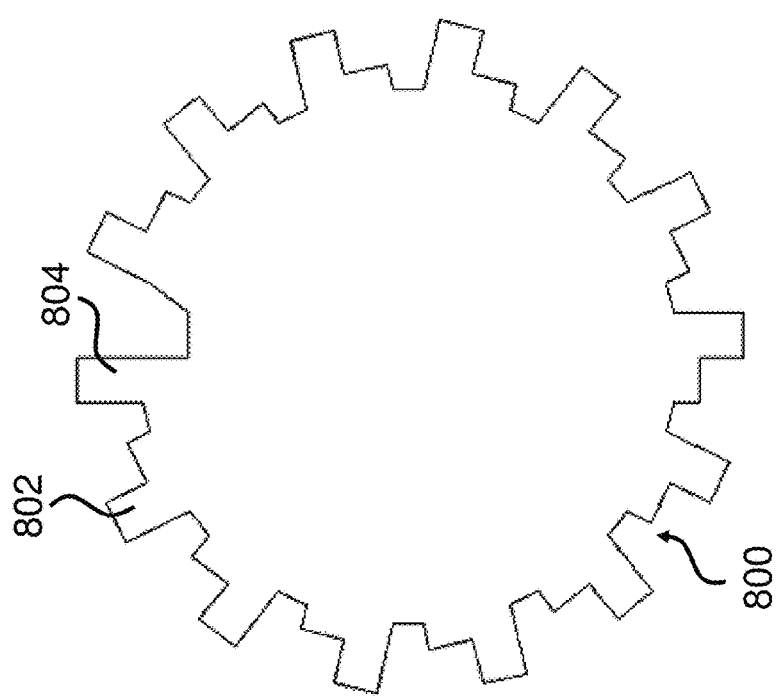
FIG. 8A shows an exemplary microcarrier that includes an asymmetric start position as an orientation indicator.

Turning now to FIG. 8A, another exemplary microcarrier 800 is shown. Like microcarrier 700, microcarrier 800 includes non-transparent polymer layer 802 (and optionally, a magnetic layer such as layer 704). In addition, microcarrier 800 includes start position 804, which has a different shape than the rest of the perimeter of microcarrier 800. Start position 804 may be used as an orientation indicator for image recognition, as described above in reference to gap 210 shown in FIG. 2A.

Figure 8B:
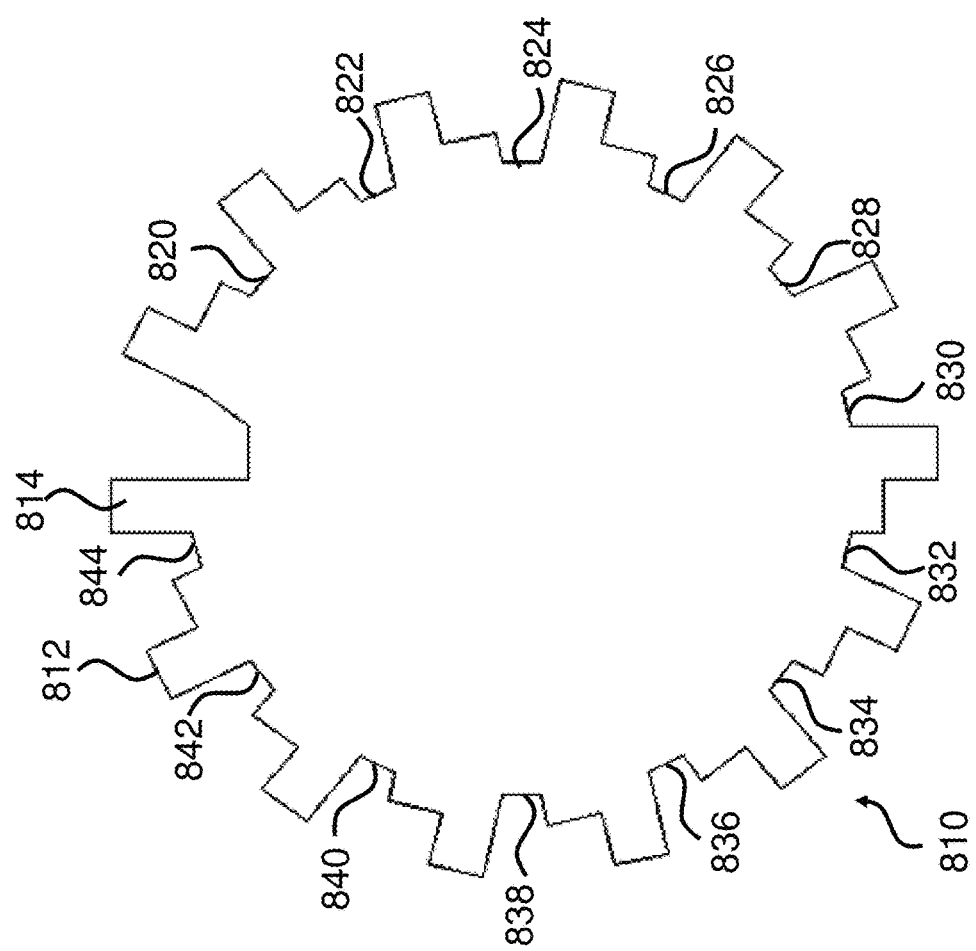
FIG. 8B shows an exemplary analog encoding scheme that includes multiple shape variation points for generating unique analog codes.

FIG. 8B illustrates a coding scheme that may be used. FIG. 8B shows microcarrier 810, which like microcarrier 800 includes non-transparent polymer layer 812 and start position 814 (and optionally, a magnetic layer such as layer 704). In this scheme, potential shape variation points around the gear are labeled, e.g., at positions 820, 822, 824, 826, 828, 830, 832, 834, 836, 838, 840, 842, and 844. As shown in FIG. 8B, even if only two potential shapes may be used for positions 820, 822, 824, 826, 828, 830, 832, 834, 836, 838, 840, 842, and 844, this embodiment allows up to $2^{13}$ unique codes. Further, as described above, the use of analog encoding greatly expands this number by allowing the use of more than two potential shapes at any or all of the indicated positions around the perimeter (e.g., at each shape variation point as labeled in FIG. 8B).

Figure 9A:
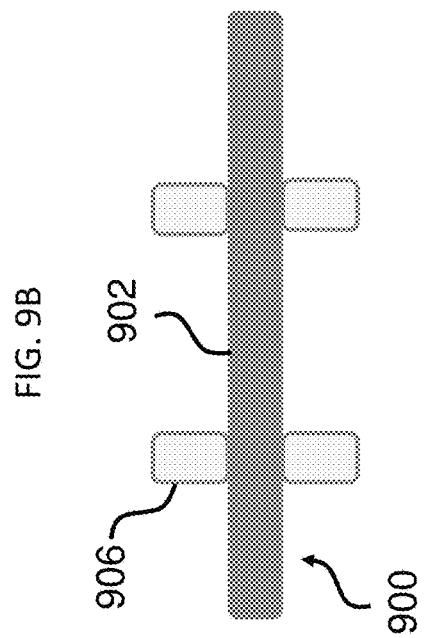
FIGS. 9A-9C show two views of an exemplary microcarrier (FIG. 9A and FIG. 9B), along with a depiction of an optional feature (FIG. 9C).
Figure 9B:
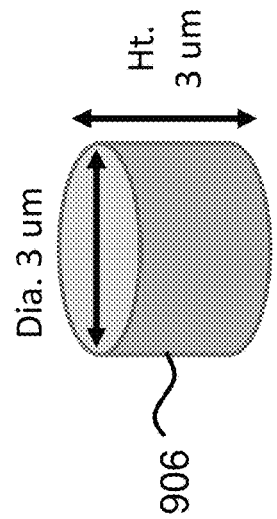
Figure 9C:
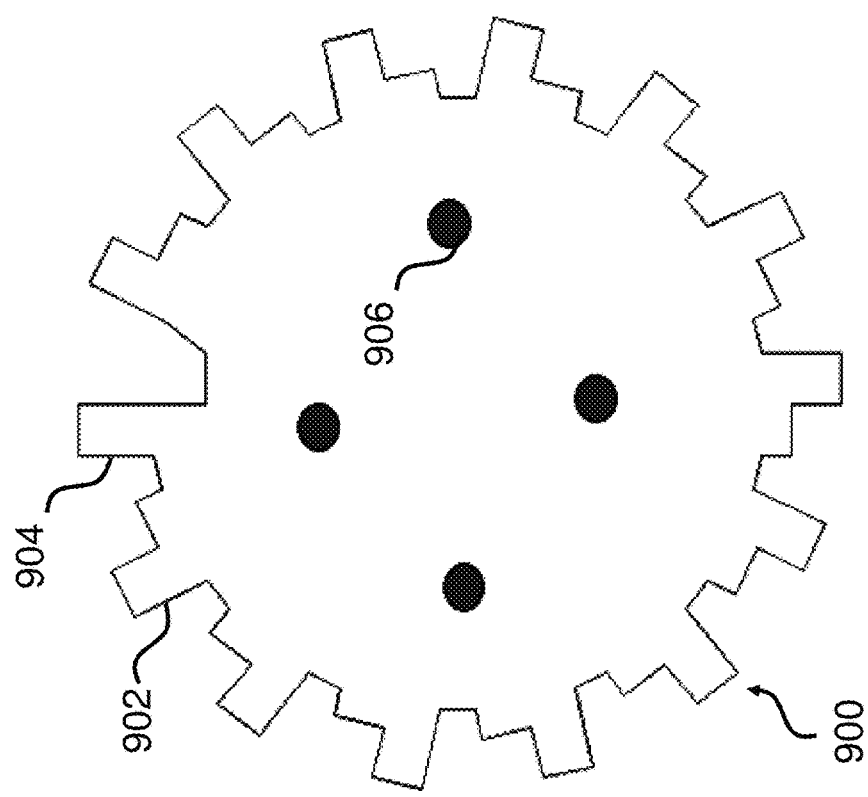

FIGS. 9A-9C illustrate yet another potential embodiment in microcarrier 900. Like microcarrier 800, microcarrier 900 is a gear-shaped microcarrier that includes non-transparent polymer layer 902 and start position 904 (and optionally, a magnetic layer such as layer 704). In addition, microcarrier 900 may have one or more columns (e.g., column 906) affixed to one or both surfaces of microcarrier 900. As shown in the cross-section in FIG. 9B, column 906 extends from a surface of layer 902. Advantageously, column 906 helps to reduce the potential for optical contact bonding (as described above in reference to column 510).

FIG. 9C illustrates the dimensions of column 906. In this example, column 906 is a cylinder 3 μm in height and 3 μm in diameter, although as described above such columns are in no way limited to a cylindrical shape. In some embodiments, column 906 is made of a magnetic material, such as nickel. This allows column 906 to function additionally as a magnetic element for magnetic manipulation of microcarrier 900, as described above.

Example 3: Methods of Producing Microcarriers with a Two-Dimensional, Analog Code Encoded in the Microcarrier Shape Having described exemplary embodiments of multiple types of microcarriers in the previous Examples, attention is now directed to methods of producing microcarriers. As described above, the microcarriers of the present disclosure may be made of one, two, or more constituent layers, depending on the desired configuration and/or optional features.

Figure 10:
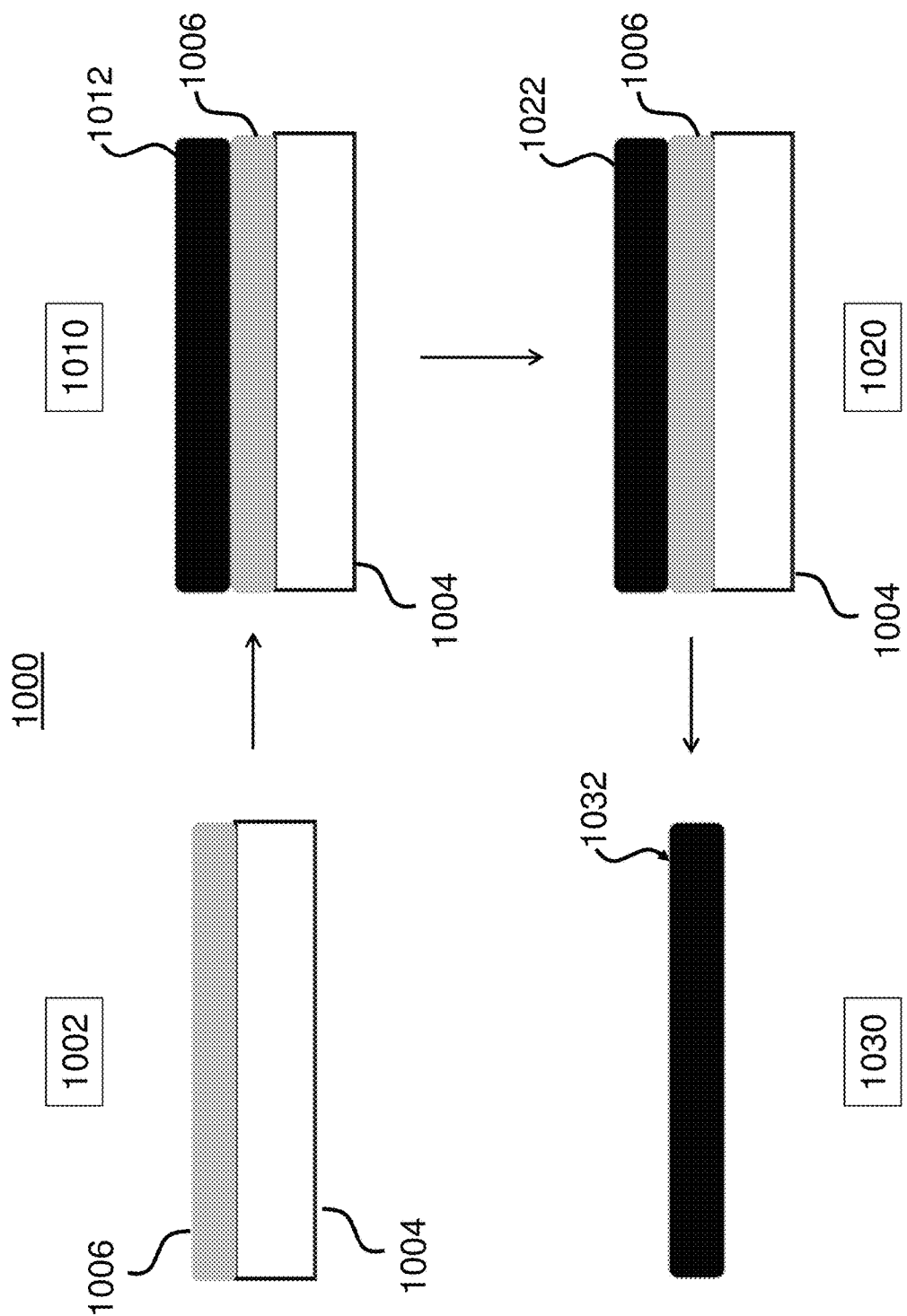
FIG. 10 shows a method for producing an exemplary microcarrier.

Process 1000 shown in FIG. 10 illustrates an exemplary workflow for manufacturing a single layer microcarrier, such as those described in Example 2 above. At block 1002, sacrificial layer 1006 is constructed on substrate 1004. In some embodiments, substrate 1004 may be a glass substrate. At block 1010, layer 1012 is deposited on sacrificial layer 1006. In some embodiments, layer 1012 is a non-transparent polymer layer. At block 1020, the perimeter of layer 1012 is shaped into a gear shape (as described above) using lithography to generate gear-shaped layer 1022. At block 1030, the entire structure (i.e., layer 1022, sacrificial layer 1006, and substrate 1004) is immersed in a solvent. This solvent treatment dissolves sacrificial layer 1006 and releases gear-shaped layer 1022 from substrate 1004, thereby generating microcarrier 1032. In some embodiments, microcarrier 1032 may be further modified, for example, by coupling a capture agent to one or both surfaces.

As described in Example 2 above, gear-shaped microcarriers may include optional elements such as magnetic components (e.g., columns and/or magnetic layers). Process 1100 shown in FIGS. 11A & 11B illustrates an exemplary workflow for manufacturing gear-shaped microcarriers with one or more magnetic components.

Figure 11A:
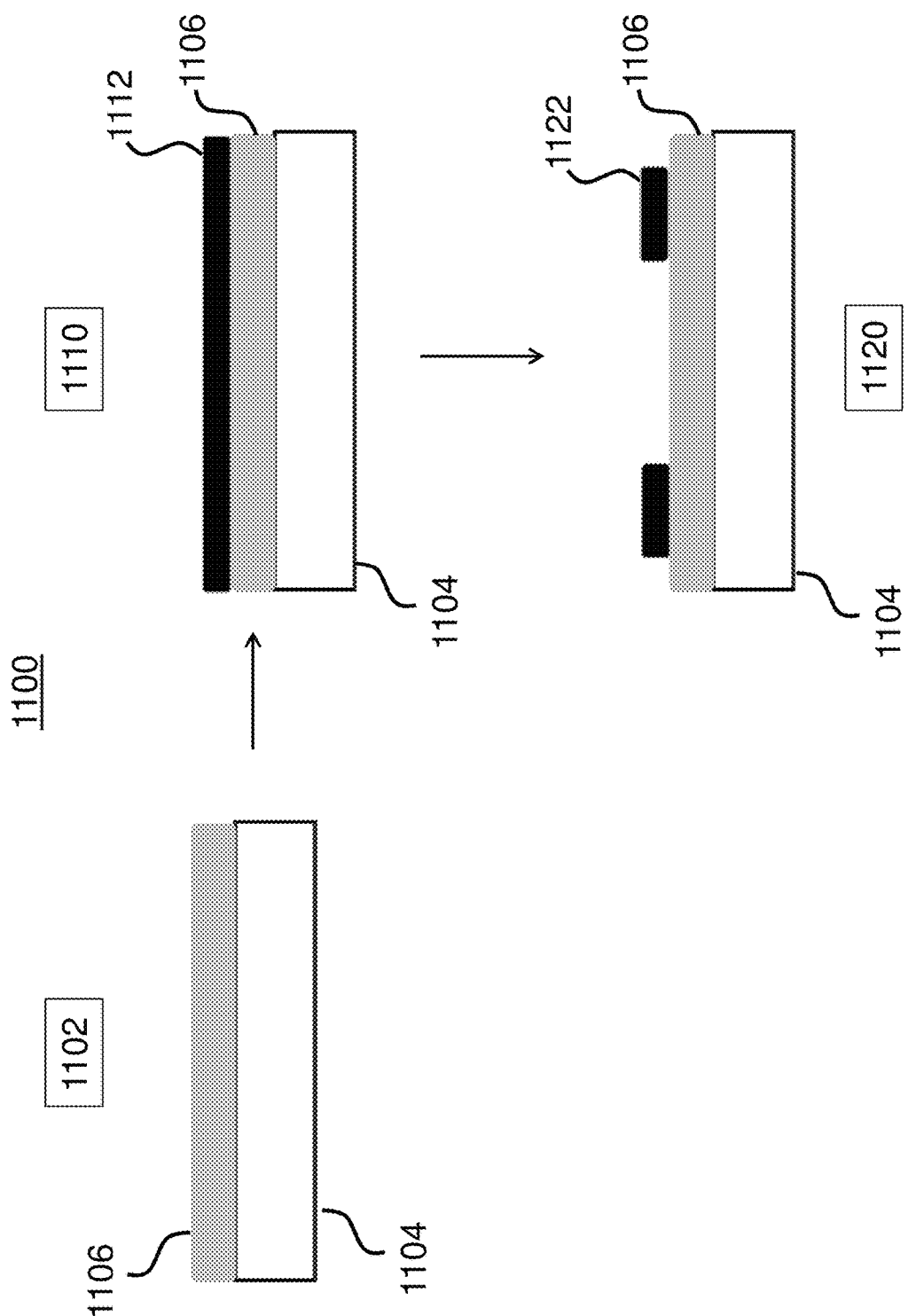
FIGS. 11A & 11B show a method for producing an exemplary microcarrier.

As shown in FIG. 11A, at block 1102, sacrificial layer 1106 is constructed on substrate 1104. In some embodiments, substrate 1104 may be a glass substrate. At block 1110, magnetic layer 1112 is deposited on sacrificial layer 1106. In some embodiments, magnetic layer 1112 includes nickel. At block 1120, magnetic layer 1112 is shaped by lithography into shaped magnetic layer 1122. Shaped magnetic layer 1122 may take any desired shape, e.g., it may be shaped into one or more columns, as illustrated in FIG. 9A with column 906.

Figure 11B:
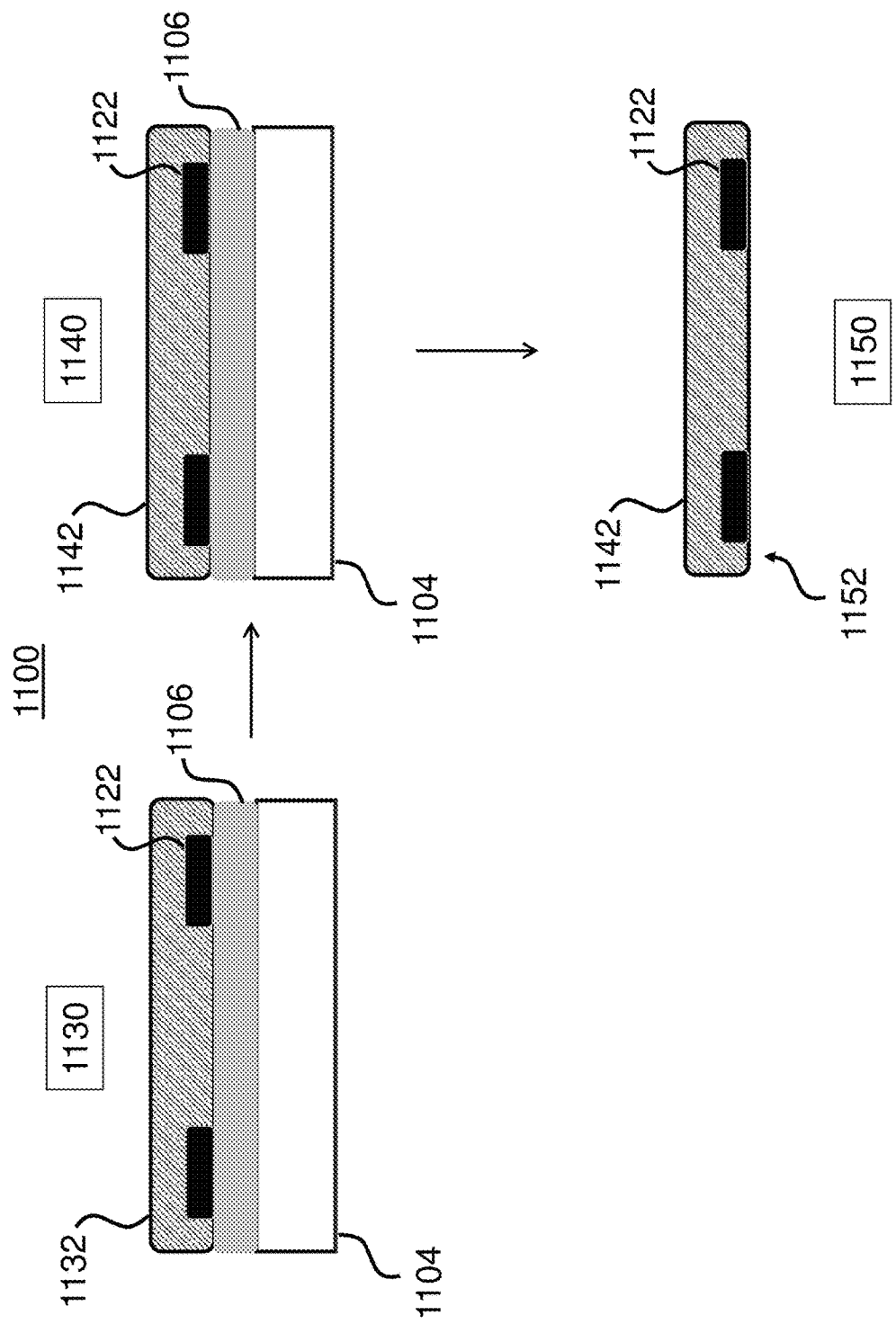

As shown in FIG. 11B, at block 1130, substantially non-transparent polymer layer 1132 is deposited over shaped magnetic layer 1122 and sacrificial layer 1106. At block 1140, the perimeter of layer 1132 is shaped by lithography into gear-shaped substantially non-transparent layer 1142 (such as one of the gear shapes illustrated in FIGS. 6A-9A). At block 1150, the entire structure (i.e., layer 1142, shaped magnetic layer 1122, sacrificial layer 1106, and substrate 1104) is immersed in a solvent. This solvent treatment dissolves sacrificial layer 1106 and releases gear-shaped layer 1142 and shaped magnetic layer 1122 from substrate 1104, thereby generating microcarrier 1152. In some embodiments, microcarrier 1152 may be further modified, for example, by coupling a capture agent to one or both surfaces.

Example 4: Methods of Producing Encoded Microcarriers with a Two-Dimensional, Analog Code and Uniform Shape Attention is now directed to methods of producing encoded microcarriers with a one or more substantially transparent and one or more substantially non-transparent polymer layers, such as those described in Example 1. FIGS. 12A-12E illustrate process 1200, an exemplary workflow for manufacturing microcarriers with a substantially transparent polymer layer, a substantially non-transparent polymer layer (whose two-dimensional shape constitutes an analog code), and one or more columns.

Figure 12A:
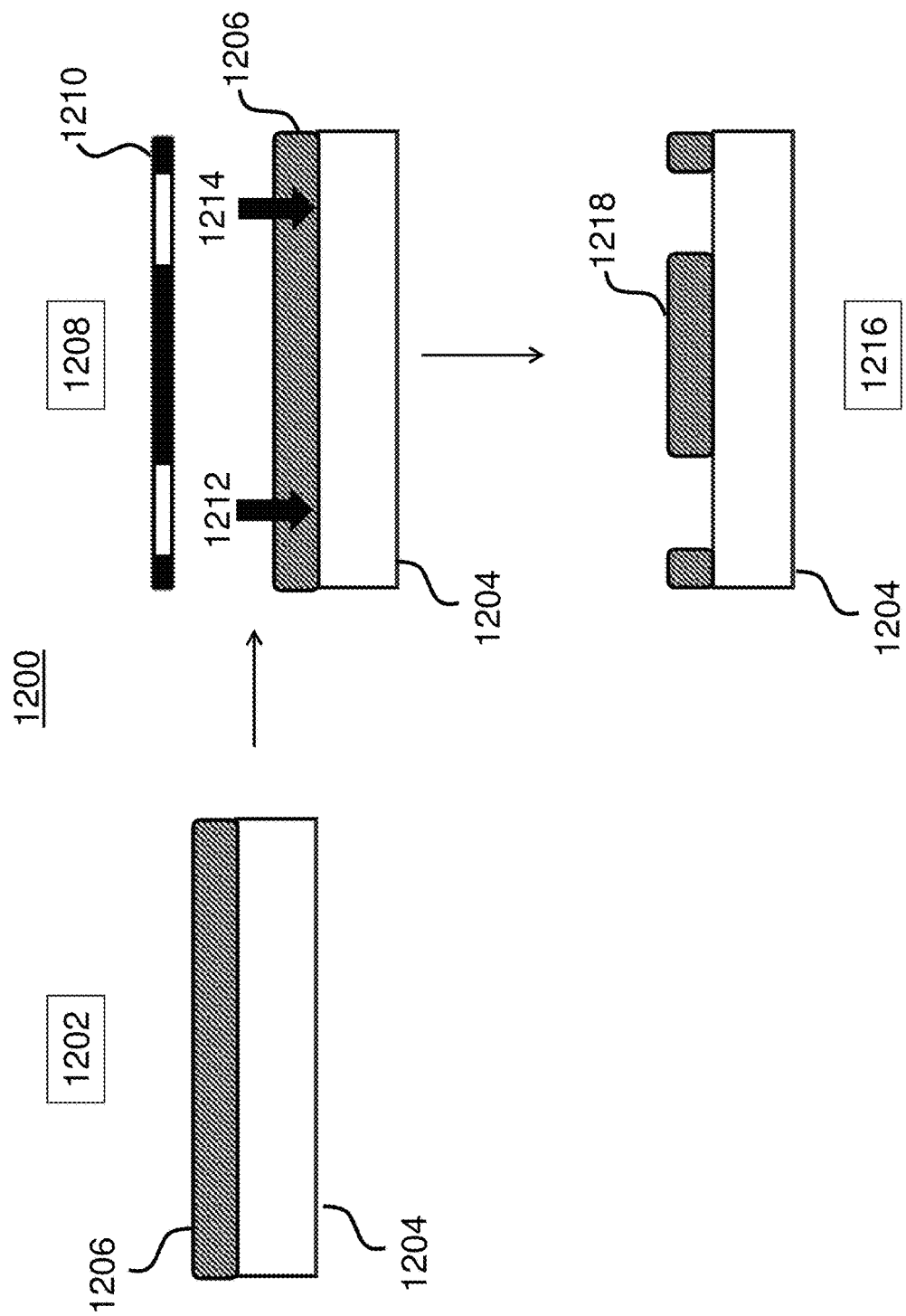
FIGS. 12A-12E show a method for producing an exemplary microcarrier.
Figure 12B:
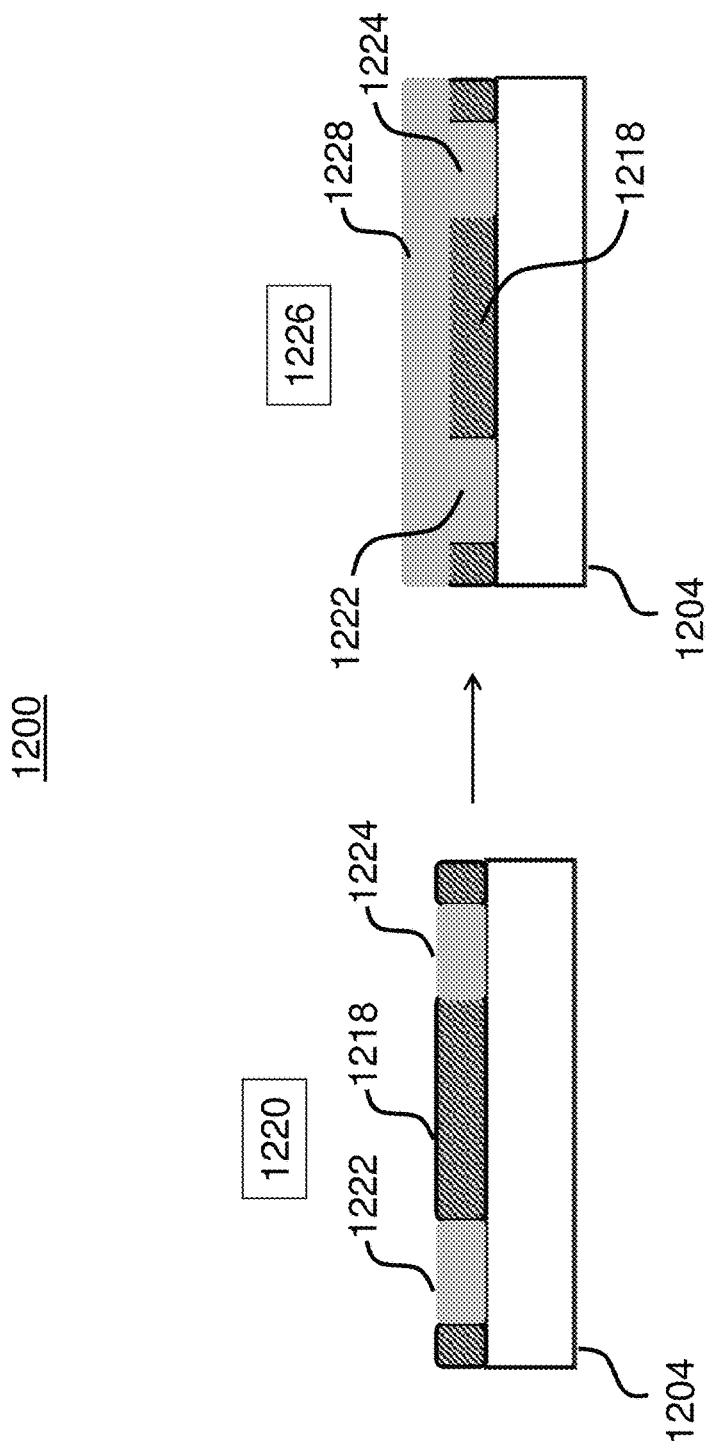
Figure 12C:
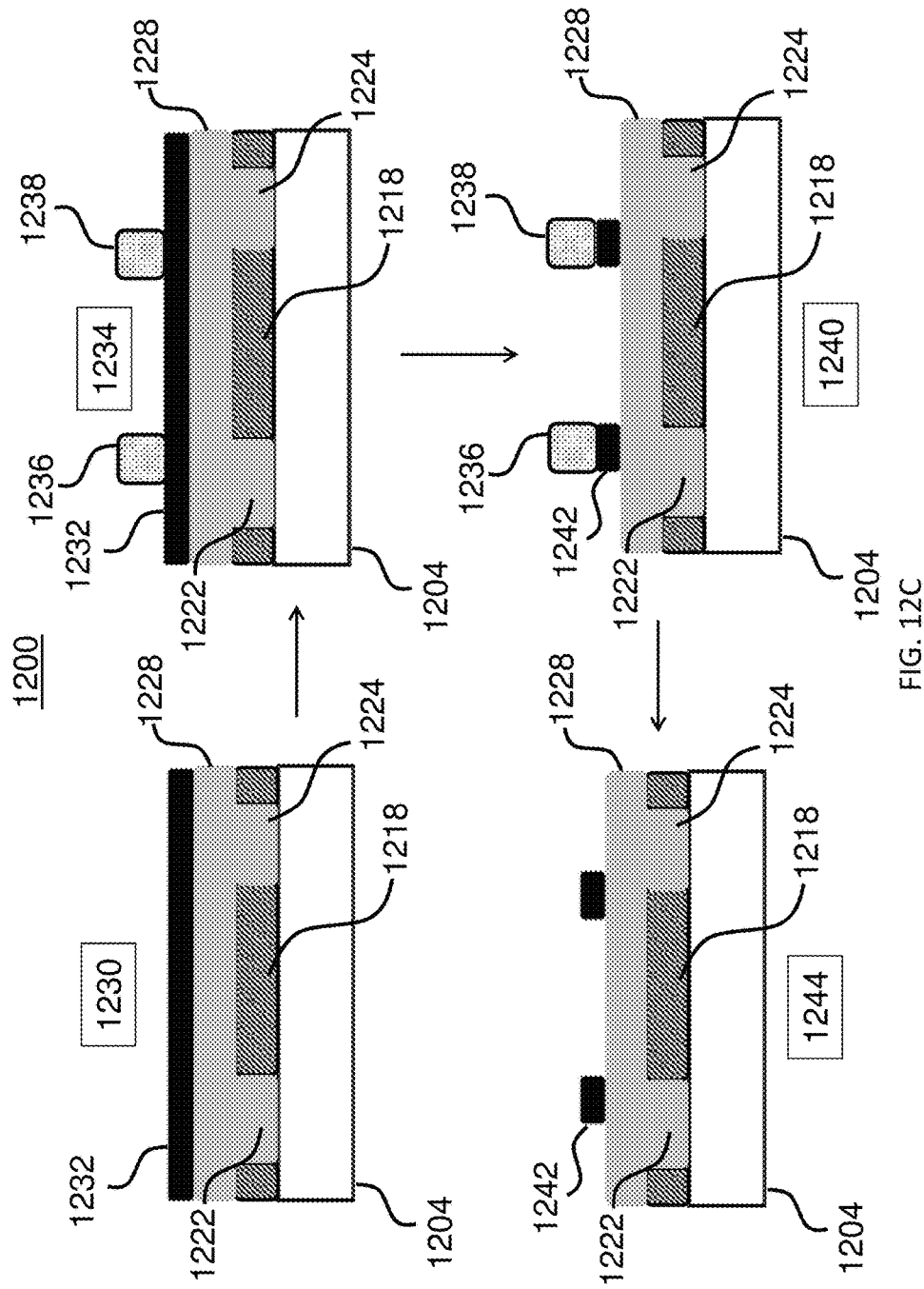
Figure 12D:
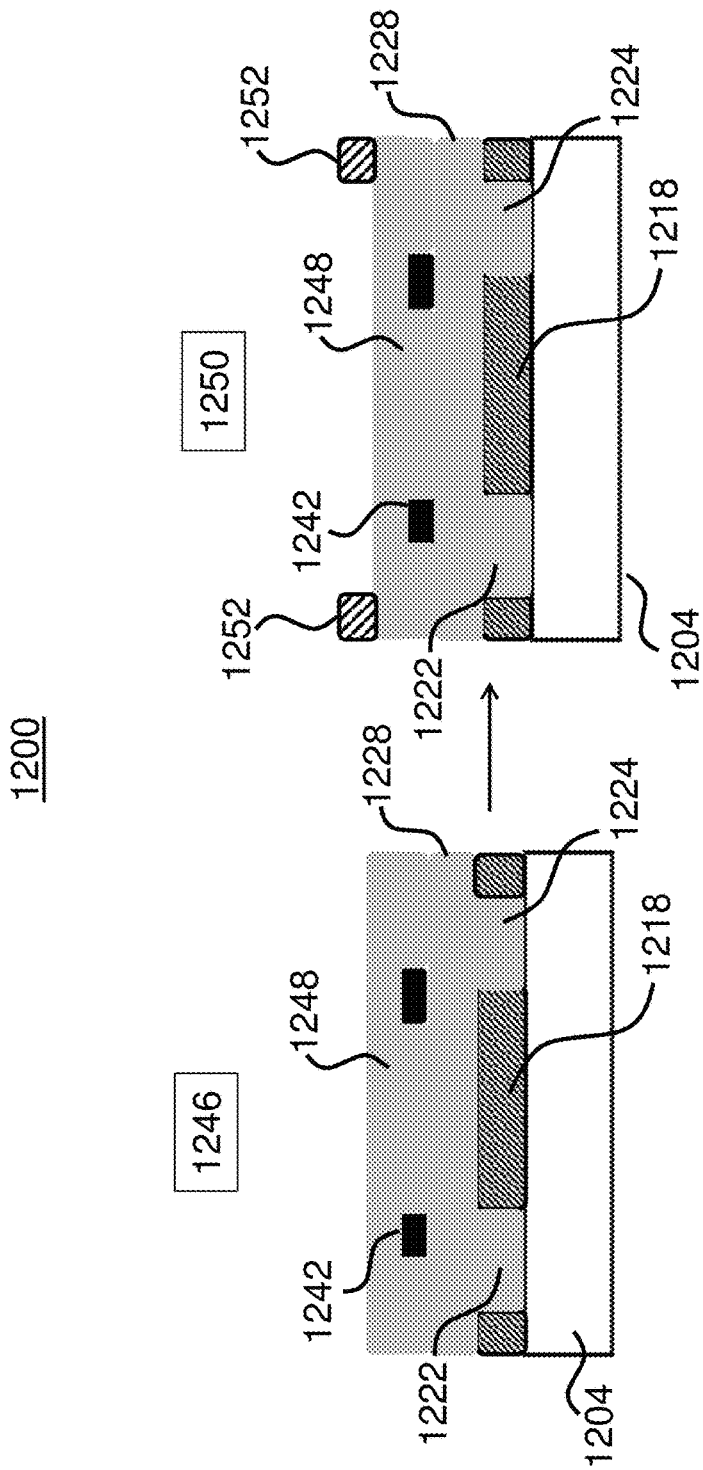
Figure 12E:
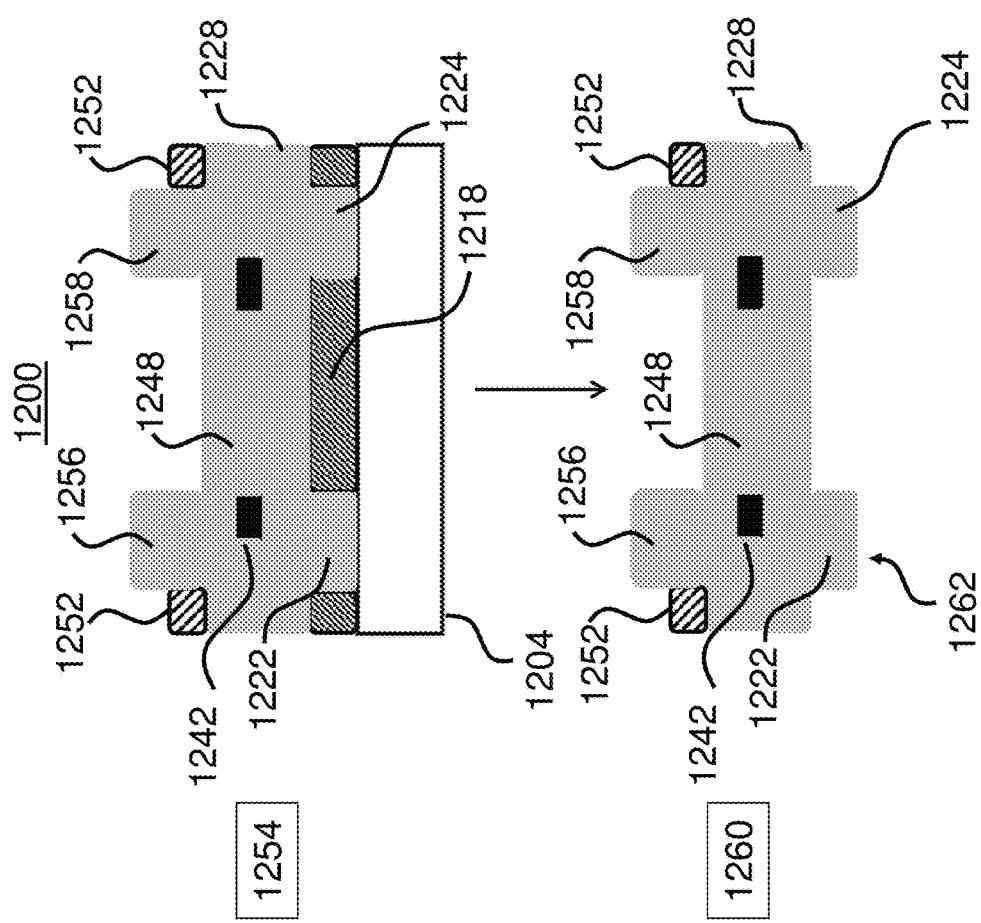

Beginning with FIG. 12A, at block 1202, sacrificial layer 1206 is deposited (e.g., by spin-coating) onto substrate 1204. In some embodiments, substrate 1204 may be a glass substrate. At block 1208, mask 1210 is applied, and sacrificial layer 1206 is exposed with UV light. UV light is applied through mask 1210, allowing UV light segments 1212 and 1214 to pass through and treat sacrificial layer 1206. At block 1216, after development of the structure through standard lithographic development, sacrificial layer 1206 is shaped into shaped sacrificial layer 1218 as a result of the masking of the UV treatment.

Process 1200 continues at block 1220 (FIG. 12B), where the masked holes in shaped sacrificial layer 1218 are filled with a substantially transparent polymer, creating columns 1222 and 1224. At block 1226, substantially transparent polymer layer 1228 is deposited over columns 1222 and 1224, as well as shaped sacrificial layer 1218.

Process 1200 continues at block 1230 (FIG. 12C), where magnetic layer 1232 is deposited over layer 1228. In some embodiments, magnetic layer 1232 includes nickel. In some embodiments, magnetic layer 1232 is deposited by sputtering. At block 1234, an etch-block layer is deposited over magnetic layer 1232, as represented by etch-blocks 1236 and 1238. At block 1240, the unblocked segments of magnetic layer 1232 are etched out, generated shaped magnetic layer 1242. In some embodiments, shaped magnetic layer 1242 may be shaped into a ring shape (with optional asymmetry for indication of orientation) surrounding a center portion of layer 1228 (see, e.g., layer 206 in FIG. 2A). At block 1244, the etch-block layer (as represented by etch-blocks 1236 and 1238) is removed.

Process 1200 continues at block 1246 (FIG. 12D), where substantially transparent polymer layer 1248 is deposited over layers 1228 and 1242 (filling in any holes in layer 1242 created by etch-blocking). At block 1250, substantially non-transparent layer 1252 is deposited and shaped by lithography on top of layer 1248. In some embodiments, layer 1252 is shaped with one or more gear teeth in a ring surrounding magnetic layer 1242 (see, e.g., layer 204 in relation to layers 202 and 206 and center portion 208 of FIG. 2A).

Process 1200 continues at block 1254 (FIG. 12E), where columns 1256 and 1258 are shaped by lithography on top of layer 1248. In some embodiments, columns 1256 and 1258 are made of a substantially transparent polymer. In some embodiments, the columns are positioned as shown in FIGS. 5A & 5B. At block 1260, substrate 1204 is cut into one or more microcarriers of the same shape (i.e., although for simplicity of explanation only one microcarrier is depicted in FIGS. 12A-12E, more than 1 microcarrier may be constructed on substrate 1204 in process 1200). Also at block 1260, the entire structure (i.e., including 1204, 1218, 1222, 1224, 1228, 1242, 1248, 1252, 1256, and 1258) is immersed in a solvent. This solvent treatment dissolves sacrificial layer 1218 and releases microcarrier 1262 from substrate 1204. In some embodiments, microcarrier 1262 may be further modified, for example, by coupling a capture agent to one or both surfaces.

Figure 13A:
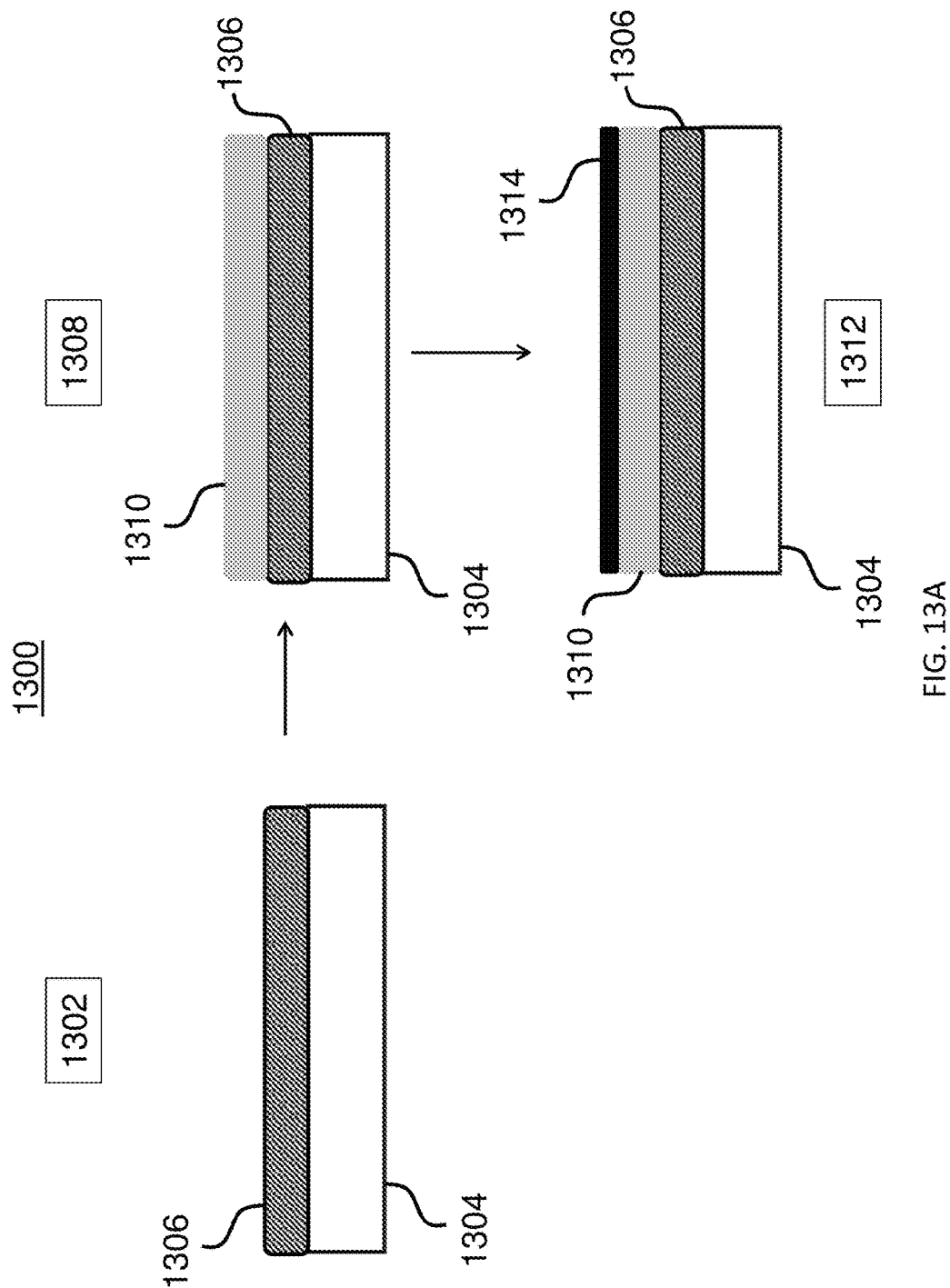
Figure 13B:
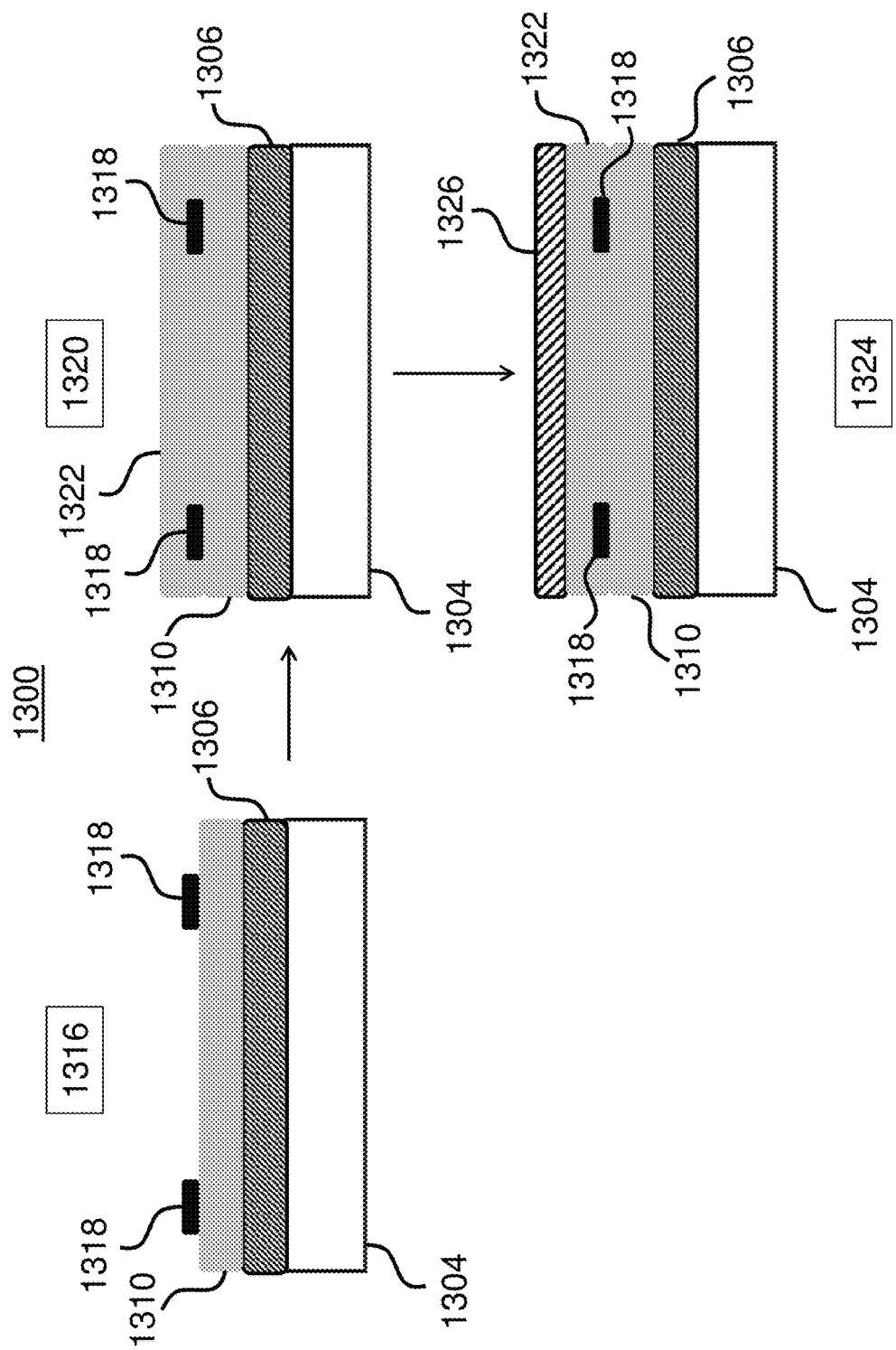

FIGS. 13A-13C illustrate process 1300, an exemplary workflow for generating a different type of multi-layer microcarrier. Beginning with FIG. 13A, at block 1302, sacrificial layer 1306 is deposited on substrate layer 1304. In some embodiments, substrate 1304 is a glass substrate. At block 1308, substantially transparent layer 1310 is deposited over sacrificial layer 1306. At block 1312, magnetic layer 1314 is deposited over layer 1310. In some embodiments, magnetic layer 1314 includes nickel.

Process 1300 continues at block 1316 (FIG. 13B), where magnetic layer 1314 is defined into shaped magnetic layer 1318. In some embodiments, shaped magnetic layer 1318 is defined into a ring shape (with optional asymmetry for indication of orientation) surrounding a center portion of layer 1310 (see, e.g., layer 206 in FIG. 2A). At block 1320, substantially transparent layer 1322 is deposited over layers 1318 and 1310, filling in any holes created by defining shaped layer 1318. At block 1324, substantially non-transparent polymer layer 1326 is deposited over layer 1322.

Process 1300 continues at block 1328 (FIG. 13C), where substantially non-transparent polymer layer 1326 is shaped by lithography into gear-shaped substantially non-transparent polymer layer 1330. In some embodiments, layer 1330 is shaped with one or more gear teeth in a ring surrounding shaped magnetic layer 1318 (see, e.g., layer 204 in relation to layers 202 and 206 and center portion 208 of FIG. 2A). At block 1332, the entire structure (i.e., including 1304, 1306, 1310, 1318, 1322, and 1330) is immersed in a solvent. This solvent treatment dissolves sacrificial layer 1306 and releases microcarrier 1334 from substrate 1304. In some embodiments, microcarrier 1334 may be further modified, for example, by coupling a capture agent to one or both surfaces.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An encoded microcarrier, comprising: (a) a first substantially transparent polymer layer having a first surface and a second surface, the first and the second surfaces being parallel to each other; (b) a substantially non-transparent polymer layer that constitutes a two-dimensional shape, wherein the substantially non-transparent polymer layer is affixed to the first surface of the first substantially transparent polymer layer and encloses a center portion of the first substantially transparent polymer layer, and wherein the two-dimensional shape of the substantially non-transparent polymer layer represents an analog code; (c) a capture agent for capturing an analyte, wherein the capture agent is not coupled to at least one of the first surface and the second surface of the first substantially transparent polymer layer in at least the center portion of the first substantially transparent polymer layer; and (d) a magnetic, substantially non-transparent layer that encloses the center portion of the first substantially transparent polymer layer between the substantially non-transparent polymer layer and the center portion of the first substantially transparent polymer layer, wherein the magnetic, substantially non-transparent layer is affixed to the first surface or the second surface of the substantially transparent polymer layer and wherein the microcarrier is less than about 50 µm in thickness.

2. The microcarrier of claim 1, further comprising: (e) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and wherein the magnetic, substantially non-transparent layer is affixed to the second surface of the first substantially transparent polymer layer, between the first and the second substantially transparent polymer layers.

3. The microcarrier of claim 2, wherein the magnetic, substantially non-transparent layer comprises nickel.

4. The microcarrier of claim 2, wherein the magnetic, substantially non-transparent layer is between about 50 nm and about 10 µm in thickness.

5. The microcarrier of claim 4, wherein the magnetic, substantially non-transparent layer is about 0.1 µm in thickness.

6. The microcarrier of claim 1, further comprising an orientation indicator for orienting the analog code of the substantially non-transparent polymer layer.

7. The microcarrier of claim 6, wherein the orientation indicator comprises an asymmetry of the magnetic, substantially non-transparent layer.

8. The microcarrier of claim 1, wherein the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality.

9. The microcarrier of claim 8, wherein the plurality of gear teeth comprises one or more gear teeth that are between about 1 pm and about 10 pm wide.

10. The microcarrier of claim 8, wherein the plurality of gear teeth comprises one or more gear teeth that are between about 1 pm and about 10 pm tall.

11. The microcarrier of claim 8, wherein the plurality of gear teeth comprises two or more gear teeth that are spaced between about 1 pm and about 10 pm apart.

12. The microcarrier of claim 1, further comprising: (f) one or more columns projecting from the first surface of the first substantially transparent polymer layer, wherein the one or more columns are not within the center portion of the first substantially transparent polymer layer; and/or (g) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer.

13. The microcarrier of claim 1, wherein the microcarrier is a substantially circular disc.

14. The microcarrier of claim 1, wherein the center portion of the first substantially transparent polymer layer comprises between about 5% and about 90% of the surface area of the first substantially transparent polymer layer.

15. The microcarrier of claim 14, wherein the center portion of the first substantially transparent polymer layer comprises about 25% of the surface area of the first substantially transparent polymer layer.

16. The microcarrier of claim 1, wherein the microcarrier is less than about 200 pm in diameter.

17. The microcarrier of claim 16, wherein the microcarrier is about 50 pm in diameter.

18. The microcarrier of claim 1, wherein the microcarrier is about 10 µm in thickness.

19. The microcarrier of claim 1, wherein the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment.

20. The microcarrier of claim 1, wherein the capture agent for capturing the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment.

21. The microcarrier of claim 1, wherein the substantially transparent polymer of the first or the second substantially transparent polymer layer comprises an epoxy-based polymer.

22. The microcarrier of claim 21, wherein the epoxy-based polymer is SU-8.

23. A method for detecting two or more analytes in a solution, comprising: (a) contacting a solution comprising a first analyte and a second analyte with a plurality of microcarriers according to claim 1, wherein the plurality of microcarriers comprises at least: (i) a first microcarrier that specifically captures the first analyte, wherein the first microcarrier is encoded with a first analog code; and (ii) a second microcarrier that specifically captures the second analyte, wherein the second microcarrier is encoded with a second analog code, and wherein the second analog code is different from the first analog code; (b) decoding the first analog code and the second analog code using analog shape recognition to identity the first microcarrier and the second microcarrier; and (c) detecting an amount of the first analyte bound to the first microcarrier and an amount of the second analyte bound to the second microcarrier.

24. The method of claim 23, wherein decoding the first analog code and the second analog code comprises: (i) illuminating the first and second microcarriers by passing light through the substantially transparent portions of the first and second microcarriers and/or the surrounding solution, wherein the light fails to pass through the substantially non-transparent portions of the first and second microcarriers to generate a first analog-coded light pattern corresponding to the first microcarrier and a second analog-coded light pattern corresponding to the second microcarrier; (ii) imaging the first analog-coded light pattern to generate a first analog-coded image and imaging the second analog-coded light pattern to generate a second analog-coded image; and (iii) using analog shape recognition to match the first analog-coded image with the first analog code and to match the second analog-coded image with the second analog code.

25. The method of claim 23, wherein detecting the amount of the first analyte bound to the first microcarrier and the amount of the second analyte bound to the second microcarrier comprises: (i) after step (a), incubating the first and the second microcarriers with a detection agent, wherein the detection agent binds the first analyte captured by the first microcarrier and the second analyte captured by the second microcarrier; and (ii) measuring the amount of detection agent bound to the first and the second microcarriers.

26. The method of claim 24, wherein the solution comprises a biological sample.

27. A kit for conducting a multiplex assay comprising a plurality of microcarriers according to claim 1, wherein the plurality of microcarriers comprises at least: (a) a first microcarrier that specifically captures a first analyte, wherein the first microcarrier is encoded with a first analog code; and (b) a second microcarrier that specifically captures a second analyte, wherein the second microcarrier is encoded with a second analog code, and wherein the second analog code is different from the first analog code.

28. The kit of claim 27, further comprising a detection agent for detecting an amount of the first analyte bound to the first microcarrier and an amount of the second analyte bound to the second microcarrier.

* * * * *